United States Patent [19]

Davis

[11] Patent Number: 4,708,809

[45] Date of Patent: Nov. 24, 1987

[54] TWO-CYCLE ENGINE OILS CONTAINING ALKYL PHENOLS

[75] Inventor: Kirk E. Davis, Euclid, Ohio

[73] Assignee: The Lubrizol Corporation, Wickliffe, Ohio

[21] Appl. No.: 385,990

[22] Filed: Jun. 7, 1982

[51] Int. Cl.$^4$ .......................................... C10M 135/10
[52] U.S. Cl. ................................. 252/33.4; 252/52 R; 252/51.5 A; 252/51.5 R; 252/50; 44/58
[58] Field of Search ...................... 252/52 R, 33.4, 32, 252/33, 42.7, 50, 51.5 R, 51.5 A; 44/58

[56] References Cited

U.S. PATENT DOCUMENTS

| | | | |
|---|---|---|---|
| 3,336,226 | 8/1967 | Kautsky | 252/42.7 |
| 4,053,428 | 10/1977 | Pindar et al. | 252/52 |
| 4,273,891 | 6/1981 | Pindar et al. | 252/52 R |

FOREIGN PATENT DOCUMENTS

| | | |
|---|---|---|
| 2031357 | 11/1970 | France . |
| WO84/0391 | 10/1984 | PCT Int'l Appl. . |
| 1212462 | 1/1969 | United Kingdom . |
| 2062672 | 5/1981 | United Kingdom . |
| 2087923 | 6/1982 | United Kingdom . |

OTHER PUBLICATIONS

Chemical Abstracts 84:491563 (1976).

*Primary Examiner*—Jacqueline V. Howard
*Attorney, Agent, or Firm*—Joseph P. Fischer; Denis A. Polyn; James L. Cordek

[57] ABSTRACT

Lubricating oils are described which are useful in two-cycle engines. These oils contain a minor amount of at least one phenolic compound of the general formula

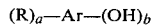

$(R)_a$—Ar—$(OH)_b$ wherein R is a substantially saturated, hydrocarbon-based group of an average of at least 10 aliphatic carbon atoms; a and b are each independently an integer of one up to three times the number of aromatic nuclei present in Ar with the proviso that the sum of a and b does not exceed the unsatisfied valences of Ar; and Ar is a single ring, a fused ring or a linked polynuclear moiety having 0 to 3 optional substituents consisting of lower alkyl, lower alkoxyl, methylol or lower hydrocarbon-based substituted methylol, halo and combinations of two or more of said optional substituents.

26 Claims, No Drawings

TWO-CYCLE ENGINE OILS CONTAINING ALKYL PHENOLS

BACKGROUND OF THE INVENTION

(1) Field of the Invention

This invention relates to lubricant compositions containing a major amount of an oil of lubricating viscosity and a minor amount of at least one alkyl phenol. The lubricants are useful in two-cycle internal combustion engines. More particularly, the invention relates to such oils containing alkyl phenols having at least one hydrocarbon-based group of at least about 10 aliphatic carbon atoms. Since two-cycle engine oils are often combined with fuels before or during use, this invention also relates to two-cycle fuel-lubricant mixtures.

(2) Prior Art

A variety of phenolic compounds have been described which are useful as lubricant and fuel additives. Alkylated amino phenols have been described in U.S. Pat. No. 4,320,021 as being useful as additives for lubricants and fuels. Amino phenol and detergent/dispersant combinations have been described in U.S. Pat. No. 4,200,545 as being useful in lubricating compositions, particularly for two-cycle internal combustion engines and also as additives and lubricant-fuel mixtures for two-cycle engines. Hydrocarbon-substituted methylol phenols are described in U.S. Pat. No. 4,053,428 as useful in lubricants and fuels.

(3) General Background

Over the past several decades the use of spark-ignited two-cycle (two-stroke) internal combustion engines including rotary engines such as those of the Wankel type has steadily increased. They are presently found in power lawn mowers and other power-operated garden equipment, power chain saws, pumps, electrical generators, marine outboard engines, snowmobiles, motorcycles and the like.

The increasing use of two-cycle engines coupled with increasing severity of the conditions in which they have operated has led to an increasing demand for oils to adequately lubricate such engines. Among the problems associated with lubrication of two-cycle engines are piston ring sticking, rusting, lubrication failure of connecting rod and main bearings and the general formation on the engine's interior surface of carbon and varnish deposits. The formation of varnish is a particularly vexatious problem since the build-up of varnish on piston and cylinder walls is believed to ultimately result in ring sticking which leads to failure of the sealing function of piston rings. Such seal failure causes loss of cylinder compression which is particularly damaging in two-cycle engines because they depend on suction to draw the new fuel charge into the exhausted cylinder. Thus, ring sticking can lead to deterioration in engine performance and unnecessary consumption of fuel and/or lubricant. Spark plug fouling and engine port plugging problems also occur in two-cycle engines.

The unique problems and techniques associated with the lubrication of two-cycle engines has led to the recognition by those skilled in the art of two-cycle engine lubricants as a distinct lubricant type. See, for example, U.S. Pat. Nos. 3,085,975; 3,004,837; and 3,753,905.

The invention described herein is directed to minimizing these problems through the provision of effective additives for two-cycle engine oils and oil-fuel combinations which eliminate or reduce engine varnish deposits and piston ring seal failure.

SUMMARY OF THE INVENTION

This invention comprises a lubricant composition for two-cycle engines comprising a major amount by weight of at least one oil of lubricating viscosity and a minor amount of weight of at least one phenolic compound of the formula $$(R)_a\text{---}Ar\text{---}(OH)_b \qquad \text{Formula I}$$

wherein R is a substantially saturated hydrocarbon-based group of an average at least 10 aliphatic carbon atoms; a and b are such independently an integer of one up to three times the number of aromatic nuclei present in Ar with the proviso that the sum of a and b does not exceed the unsatisfied valences of Ar; and Ar is a single ring, a fused ring or a linked polynuclear aromatic moiety having 0 to 3 optional substituents consisting of lower alkyl, lower alkoxyl, methylol or lower hydrocarbon-based substituted methylol, halo and combinations of two or more of said optional substituents.

The term "phenol" is used in this specification in its art-accepted generic sense to refer to hydroxy-aromatic compounds having at least one hydroxyl group bonded directly to a carbon of an aromatic ring.

Lubricating oil-fuel mixtures for two-cycle engines and methods for lubricating two-cycle engines including Wankel engines are also within the scope of this invention.

DESCRIPTION OF THE INVENTION

The Oils of Lubricating Viscosity

The two-cycle engine oil compositions of this invention comprise a major amount of an oil of lubricating viscosity. Typically this viscosity is in the range of about 2.0 to about 150 cst at 19.9° C., more typically in the range of about 5.0 to about 130 cst at 98.9° C.

These oils of lubricating viscosity can be natural or synthetic oils. Mixtures of such oils are also often useful.

Natural oils include mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Oils made by polymerizing olefins of less than 5 carbon atoms, such as ethylene, propylene, butylenes, isobutene, pentene, and mixtures thereof are typical synthetic polymer oils. Methods of preparing such polymer oils are well known to those skilled in the art as is shown by U.S. Pat. Nos. 2,278,445; 2,301,052; 2,318,719; 2,329,714; 2,345,574; and 2,422,443.

Alkylene oxide polymers (i.e., homopolymers, interpolymers, and derivatives thereof where the terminal hydroxyl groups have been modified by esterification, etherification, etc.) constitute a preferred class of known synthetic lubricating oils for the purpose of this invention, especially for use in combination with alkanol fuels. They are exemplified by the oils prepared through polymerization of ethylene oxide or propylene oxide, the alkyl and aryl ethers of these polyoxyalkylene polymers (e.g., methyl polypropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, de(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

The Alkyl Phenols: The Aromatic Moiety, Ar

The aromatic moiety, Ar, can be a single aromatic nucleus such as a benzene nucleus, a pyridine nucleus, a thiophene nucleus, a 1,2,3,4-tetrahydronaphthalene nucleus, etc., or a polynuclear aromatic moiety. Such polynuclear moieties can be of the fused type; that is, wherein at least two aromatic nuclei are fused at two points to another nucleus such as found in naphthalene, anthracene, the azanaphthalenes, etc. Such polynuclear aromatic moieties also can be of the linked type wherein at least two nuclei (either mono or polynuclear) are linked through bridging linkages to each other. Such bridging linkages can be chosen from the group consisting of carbon-to-carbon single bonds, ether linkages, keto linkages, sulfide linkages, polysulfide linkages of 2 to 6 sulfur atoms, sulfinyl linkages, sulfonyl linkages, methylene linkages, alkylene linkages, di-(lower alkyl)-methylene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between aromatic nuclei. For example, a fluorene nucleus has two benzene nuclei linked by both a methylene linkage and a covalent bond. Such a nucleus may be considered to have 3 nuclei but only two of them are aromatic. Normally, Ar will contain only carbon atoms in the aromatic nuclei per se.

The number of aromatic nuclei, fused, linked or both, in Ar can play a role in determining the values of a and b in Formula I. For example, when Ar contains a single aromatic nucleus, a and b are each independently 1 to 3. When Ar contains 2 aromatic nuclei, a and b can each be an integer of 1 to 6 that is, from 1 up to three times the number of aromatic nuclei present (e.g., in naphthalene, 2 nuclei). With a trinuclear Ar moiety, a and b can again each be an integer of 1 to 9. Thus, for example, when Ar is a biphenyl moiety, a and b can each independently be an integer of 1 to 6. The values of a and b are obviously limited by the fact that their sum cannot exceed the total unsatisfied valences of Ar.

The single ring aromatic nucleus which can be the Ar moiety can be represented by the general formula

wherein ar represents a single ring aromatic nucleus (e.g., benzene) of 4 to 10 carbons, each Q independently represents a lower alkyl group, lower alkoxyl group, methylol or lower hydrocarbon-based substituted methylol, or halogen atom, and m is 0 to 3. As used in this specification and appended claims, "lower" refers to groups having 7 to less carbon atoms such as lower alkyl and lower alkoxyl groups. Halogen atoms include fluorine, chlorine, bromine and iodine atoms; usually, the halogen atoms are fluorine and chlorine atoms.

Specific examples of such single ring Ar moieties are the following:

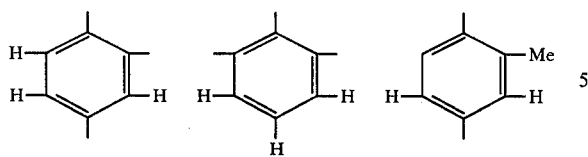
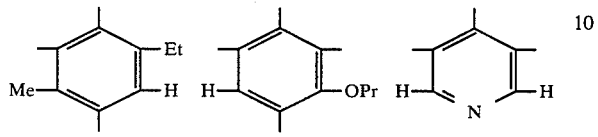
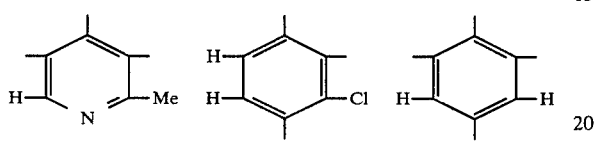
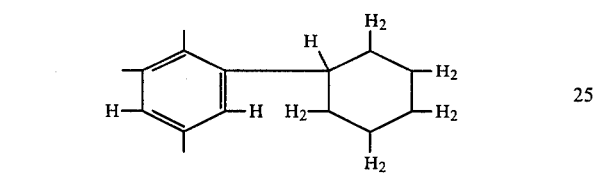
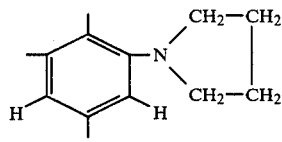

wherein Me is methyl, Et is ethyl, and Pr is n-propyl.

When Ar is a polynuclear fused-ring aromatic moiety, it can be represented by the general formula

wherein ar, Q and m are as defined hereinabove, m' is 1 to 4 and ⌬ represent a pair of fusing bonds fusing two rings so as to make two carbon atoms part of the rings of each of two adjacent rings. Specific examples of fused ring aromatic moieties Ar include:

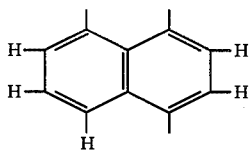

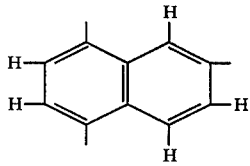

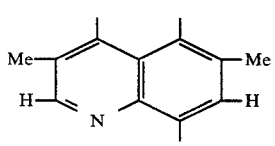

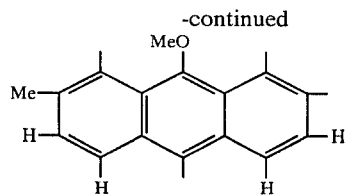

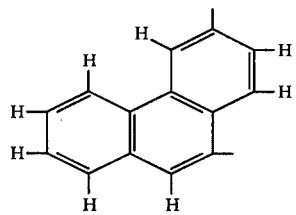

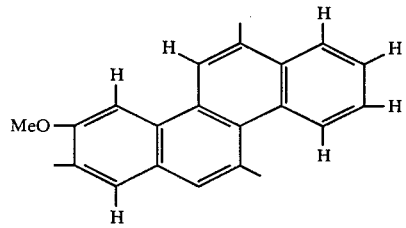

When the aromatic moiety Ar is a linked polynuclear aromatic moiety it can be represented by the general formula $$ar(-Lng-ar-)_w(Q)_{mw}$$

wherein w is an integer of 1 to about 20, ar is as described above with the proviso that there are at least 3 unsatisfied (i.e., free) valences in the total of ar groups, Q and m are as defined hereinbefore, and each Lng is a bridging linkage individually chosen from the group consisting of carbon-to-carbon single bonds, ether linkages (e.g., —CH$_2$—O—CH$_2$—), keto linkages (e.g., $$-\overset{O}{\underset{\|}{C}}-),$$

sulfide linkages (e.g., —S—), polysulfide linkages of 2 to 6 sulfur linkages (e.g., —S$_{2-6}$—), sulfinyl linkages (e.g., —S(O)—), sulfonyl linkages (e.g., —S(O)$_2$—), lower alkylene linkages (e.g., —CH$_2$—, —CH$_2$—CH$_2$—, —CH—O(R$^o$)H—, etc.), di(lower alkyl)-methylene linkages (e.g., —CR$_2^o$), lower alkylene ether linkages (e.g., —CH$_2$O—, —CH$_2$O—CH$_2$—, —CH$_2$—CH$_2$O—, —CH$_2$CH$_2$OCH$_2$CH$_2$—, $$-\underset{R^o}{\overset{|}{CH_2CHOCH_2CH}}-,\quad -\underset{R^o\ R^o}{\overset{|\ \ |}{CH_2CHOCHCH_2}}-,$$

etc.), lower alkylene keto linkages (e.g., $$-CH_2\overset{O}{\underset{\|}{C}}-,\quad -CH_2\overset{O}{\underset{\|}{C}}CH_2-),$$

lower alkylene sulfide linkages (e.g., wherein one or more —O—'s in the lower alkylene ether linkages is replaced with an —S— atom), lower alkylene polysulfide linkages (e.g., wherein one or more —O—'s is replaced with a —S$_{2-6}$ group) amino linkages (e.g.,

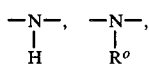

—CH$_2$N—, —CH$_2$NCH$_2$—, —alk—N—, where alk is lower alkylene, etc.), polyamino linkages (e.g., —N-(alkN)$_{1-10}$, where the unsatisfied free N valences are taken up with H atoms or R$^o$ groups), and mixtures of such bridging linkages (each R$^o$ being a lower alkyl group).

Specific examples of Ar when it is linked polynuclear aromatic moiety include:

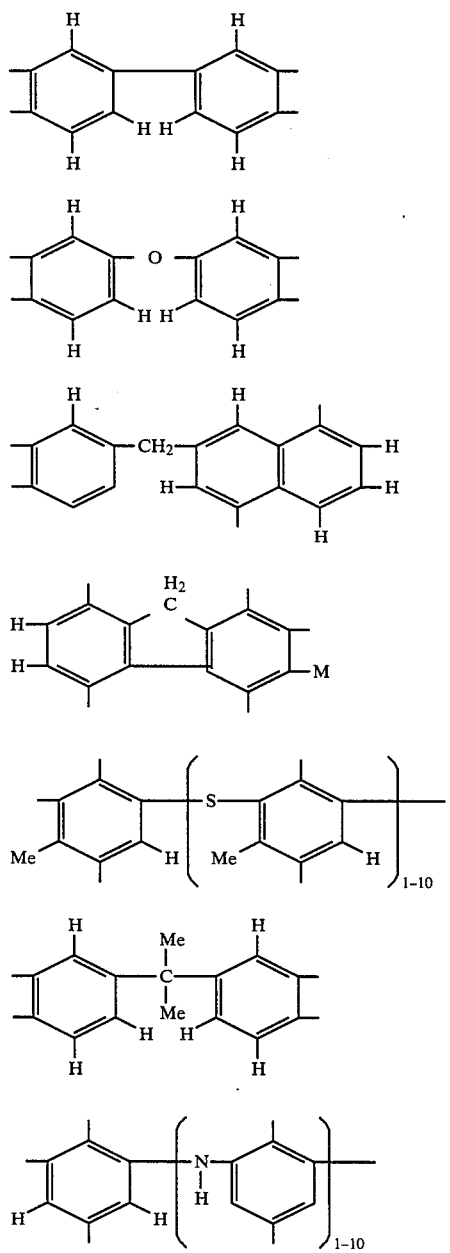

Usually all these Ar moeties are unsubstituted except for the R and —OH groups (and any bridging groups).

For such reasons as cost, availability, performance etc., the Ar moiety is normally a benzene nucleus, lower alkylene bridged benzene nucleus, or a naphthalene nucleus. Thus, a typical Ar moiety is a benzene or naphthalene nucleus having 3 to 5 unsatisfied valences, so that one or two of said valences may be satisfied by a hydroxyl group with the remaining unsatisfied valences being, insofar as possible, either ortho or para to a hydroxyl group. Preferably, Ar is a benzene nucleus having 3 to 4 unsatisfied valences so that one can be satisfied by a hydroxyl group with the remaining 2 or 3 being either ortho or para to the hydroxyl group.

The Substantially Saturated Hydrocarbon-based Group R

The phenolic compounds used in the two-cycle oils of the present invention contain, directly bonded to the aromatic moiety Ar, a substantially saturated monovalent hydrocarbon-based group R of at least about 10 aliphatic carbon atoms. This R group preferably contains at least 30 and up to about 400 aliphatic carbon atoms. More than one such group can be present, but usually, no more than 2 or 3 such groups are present for each aromatic nucleus in the aromatic moiety Ar. The total number of R groups present is indicated by the value for "a" in Formula I. Usually, the hydrocarbon-based group has at least about 30, more typically, at least about 50 aliphatic carbon atoms and up to about 400, more typically, up to about 300 aliphatic carbon atoms.

Illustrative hydrocarbon based groups containing at least ten carbon atoms are n-decyl, n-dodecyl, tetrapropenyl, n-octadecyl, oleyl, chlorooctadecyl, triicontanyl, etc. Generally, the hydrocarbon-based groups R are made from homo- or interpolymers (e.g., copolymers, terpolymers) of mono- and diolefins having 2 to 10 carbon atoms, such as ethylene, propylene, butene-1, isobutene, butadiene, isoprene, 1-hexene, 1-octene, etc. Typically, these olefins are 1-monoolefins. The R groups can also be derived from the halogenated (e.g., chlorinated or brominated) analogs of such homo- or interpolymers. The R groups can, however, be made from other sources, such as monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. Any unsaturation in the R groups may be reduced or eliminated by hydrogenation according to procedures known in the art.

As used herein, the term "hydrocarbon-based" denotes a group having a carbon atom directly attached to the remainder of the molecule and having a predominantly hydrocarbon character within the context of this invention. Therefore, hydrocarbon-based groups can contain up to one non-hydrocarbon radical for every ten carbon atoms provided this non-hydrocarbon radical does not significantly alter the predominantly hydrocarbon character of the group. Those skilled in the art will be aware of such radicals, which include, for example, hydroxyl, halo (especially chloro and fluoro), alkoxyl, alkyl mercapto, alkyl sulfoxy, etc. Usually, however, the hydrocarbon-based groups R are purely hydrocarbyl and contain no such non-hydrocarbyl radicals.

The hydrocarbon-based groups R are substantially saturated, that is, they contain no more than one carbon-to-carbon unsaturated bond for every ten carbon-to-carbon single bonds present. Usually, they contain no more than one carbon-to-carbon non-aromatic unsaturated bond for every 50 carbon-to-carbon bonds present.

The hydrocarbon-based groups of the phenols used in the two-cycle oils of this invention are also substantially aliphatic in nature, that is, they contain no more than one non-aliphatic moiety (cycloalkyl, cycloalkenyl or aromatic) group of six or less carbon atoms for every ten carbon atoms in the R group. Usually, however, the R groups contain no more than one such non-aliphatic group for every fifty carbon atoms, and in many cases, they contain no such non-aliphatic groups at all; that is, the typical R groups are purely aliphatic. Typically, these purely aliphatic R groups are alkyl or alkenyl groups.

Specific examples of the substantially saturated hydrocarbon-based R groups containing an average of more than 30 carbon atoms are the following:
- a mixture of poly(ethylene/propylene) groups of about 35 to about 70 carbon atoms
- a mixture of the oxidatively or mechanically degraded poly(ethylene/propylene) groups of about 35 to about 70 carbon atoms
- a mixture of poly(propylene/1-hexene) groups of about 80 to about 150 carbon atoms
- a mixture of poly(isobutene) groups having an average of 50 to 75 carbon atoms A preferred source of the group R are poly(isobutene)s obtained by polymerization of a $C_4$ refinery stream having a butene content of 35 to 75 weight percent and isobutene content of 30 to 60 weight percent in the presence of a Lewis acid catalyst such as aluminum trichloride or boron trifluoride. These polybutenes contain predominantly (greater than 80% of total repeating units) isobutene repeating units of the configuration

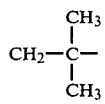

The attachment of the hydrocarbon-based group R to the aromatic moiety Ar of the phenols used in the two-cycle oils of this invention can be accomplished by a number of techniques well known to those skilled in the art. One particularly suitable technique is the Friedel-crafts reaction, wherein an olefin (e.g., a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride, etc.). Methods and conditions for carrying out such reactions are well known to those skilled in the art. See, for example, the discussion in the article entitled, "Alkylation of Phenols" in Kirk-Othmer "Encyclopedia of Chemical Technology", Second Edition, Vol. 1, pages 894–895, Interscience Publishers, a division of John Wiley and Company, N.Y., 1963. Other equally well known appropriate and convenient techniques for attaching the hydrocarbon-based group R to the aromatic moiety Ar will occur readily to those skilled in the art.

As will be appreciated from inspection of Formula I, the phenols used in the two-cycle oils of this invention contain at least one of each of the following substituents: a hydroxyl group and a R group as defined above. Each of the foregoing groups must be attached to a carbon atom which is a part of an aromatic nucleus in the Ar moiety. They need not, however, each be attached to the same aromatic ring if more than one aromatic nucleus is present in the Ar moiety.

The Optional Substituents (R'')

As mentioned, the aromatic moiety Ar may contain up to 3 optional substituents which are lower alkyl, lower alkoxyl, methylol or lower hydrocarbon-based substituted methylol, halo or combinations of two or more of these optional substituents. These substituents may be attached to a carbon atom which is part of the aromatic nucleus in Ar. They need not, however, be attached to the same aromatic ring if more than one ring is present in Ar.

A preferred substituent is a methylol or substituted methylol as defined above. The lower hydrocarbon-based substituents have up to seven carbon atoms and can be alkyl (e.g., methyl, ethyl, etc.), alkenyl (propenyl, etc.), aryl (e.g. phenyl, tolyl), and alkaryl (e.g., benzyl). They can be represented by "hyd" and the methylol substituents thus can be represented by —CH$_2$OH(methylol),

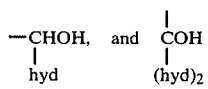

Usually the substituent is methylol itself or an alkyl-substituted methylol or phenyl-substituted methylol substituent, e.g.,

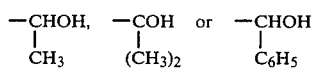

The methylol or substituted methylol group can be introduced by reaction of the phenol or alkylated phenol with a hydrocarbon-based aldehyde or functional equivalent thereof. Suitable aldehydes include formaldehyde, benzaldehyde, acetaldehyde, butyraldehyde, hydroxy butyraldehyde, hexanals, etc. "Functional equivalents" are materials (e.g., solutions, polymers, hydrates, etc.) which react as aldehydes under the conditions of the reaction and include such materials as paraformaldehyde, hexamethylenetetramine, paraldehyde, formalin and methylol. Should disubstituted methylol groups be desired, the aldehyde is replaced with an appropriate ketone, such as acetone, methyl ethyl ketone, acetophenone, benzophenone, and the like. Mixtures of aldehydes and/or ketones can also be used to produce compounds having mixtures of methylol groups.

Formaldehyde and functional equivalents are generally preferred, since they yield the preferred methylol groups. Introduction of the methylol groups usually takes place by reacting the phenolic compound with an aldehyde, ketone or functional equivalent thereof in the presence or absence of an acidic or alkaline reagent. When the reaction takes place in the absence of such reagent, usually a portion of the mixture becomes acidic or alkaline by in situ degradation of the aldehyde or ketone; excess phenol can also fulfill this function.

Generally, however, the reaction of the aldehyde, ketone or functional equivalent thereof takes place in the presence of an alkaline reagent such as an alkali metal or alkaline earth metal oxide, hydroxide or lower alkoxide, at a temperature up to about 160° C. Other alkaline reagents which can be used include sodium carbonate, sodium bicarbonate, sodium acetate, sodium propionate, pyridine, and hydrocarbon-based amines such as methyl amine and aniline; naturally, mixtures of two or more bases can be used. Preferably, the reaction takes place in the temperature range of about 30° to about 125° C.; more usually, it is carried out between 70° and 100° C.

The relative proportions of phenolic compound and aldehyde, ketone or functional equivalent thereof are not critical. It is generally satisfactory to use 0.1–5 equivalents of aldehyde and about 0.05–10.0 equivalents of alkaline reagent per equivalent of phenolic compound. As used herein, the term "equivalent" when applied to a phenolic compound indicates the weight of such compound equal to the molecular weight thereof divided by the number of unsubstituted aromatic carbons bearing hydrogen atoms. As applied to the aldehyde, ketone or functional equivalent thereof, an "equivalent" is the weight required to produce one mole of monomeric aldehyde. An equivalent of alkaline reagent is that weight of reagent which when dissolved in one liter of solvent (e.g., water) will give a one normal solution. One equivalent of alkaline reagent will therefore neutralize, i.e., bring to pH7 a one normal solution of, for example, hydrochloric or sulfuric acid.

It is generally convenient to carry out the reaction of the phenol in the presence of a substantially inert, organic liquid diluent which may be volatile or nonvolatile. This diluent may dissolve all the reactants, or it may not, but in any event, it does not substantially affect the course of the reaction under the prevailing conditions though, in certain cases, it may promote the speed of the reaction by increasing the contact of the reagents. Suitable diluents include hydrocarbons such as naphtha, textile spirits, benzene, toluene, xylene; mineral oils (which are among the preferred); synthetic oils (as described hereinbelow); alcohols, such as isopropanol, butanol, isobutanol, amyl alcohol, ethyl hexanols and the like; ethers, such as triethylene or diethylene glycol mono- or di-ethyl ether and the like, as well as mixtures of two or more of these.

The reaction of the phenolic compound with aldehyde or ketone generally takes place in 0.5 to 8 hours, depending on such factors as the reaction temperature, amount and nature of alkaline catalyst used, etc. The control of such factors is well within the skill of the art and the effect of these factors is apparent. After the reaction has been completed to the desired extent, it can be substantially stopped by neutralization of the reaction mixture when an alkaline reagent is present. This neutralization can be effected with any suitable acidic material, typically a mineral acid or an organic acid of anhydride; an acidic gas such as carbon dioxide, hydrogen sulfide, sulfur dioxide and the like, can also be used. Generally neutralization is accomplished with a carboxylic acid, especially a lower alkanoic carboxylic acid such as formic acid, acetic or propionic acid; mixtures of two or more acids can, of course, be used to accomplish the neutralization. The neutralization is carried out at a temperature of about 30° to 150° C. An amount of neutralizing agent sufficient to substantially neutralize the reaction mixture is used. Substantial neutralization means that the reaction mixture is brought to a pH ranging between 4.5 and 8.0. Usually the reaction mixture is brought to a minimum pH of about 6 or a maximum pH of about 7.5.

The reaction product, i.e., the phenolic compound, can be recovered from the reaction mixture by such techniques as filtration (for example, to remove the product of the neutralization of the alkaline reagent) followed by distillation, evaporation, etc. Such techniques are well known to those skilled in the art.

These compositions contain at least one compound which can be represented by the general formula

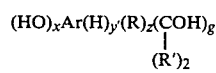
Formula II wherein x, z and g are each at least one; y' is 0 or at least one, the sum of x, y', z and g does not exceed the available valences of Ar; each R' is hydrogen or a "hyd" substituent as described above, and R is as described above.

Often, however, it is not necessary to isolate the phenolic compound formed from the reaction solvent especially if it is to blended in a fuel or lubricant.

When the reaction temperature is in the higher range, i.e., above about 100° C., substantial amounts of ether condensation productions can be formed. It is believed that these condensates have the general formula

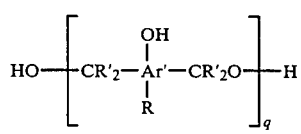
Formula III wherein q is a number ranging from 2 to about 10. These condensates thus contain alkylene ether linkages, i.e., —CR'₂O— linkages. Thus, for example, in the case of the reaction of an alkyl phenol with formaldehyde, ether condensates are formed having the general formula

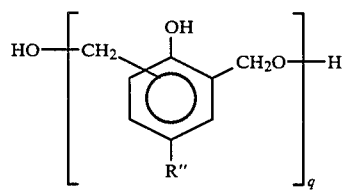
Formula IV wherein q is a number ranging from 2 to about 10 and R" is an alkyl group of at least 30 carbon atoms. It is possible that small amounts of such ether condensates accompany the predominantly larger uncondensed hydroxy aromatic compounds produced at lower temperatures.

If a strong acid, such as a mineral acid, is used for the neutralization, it is important to control the amount thereof present so as not to bring the reaction mixture to a low pH than specified hereinabove. For example, at lower pH's, over-condensation occurs to form methylene-bridged phenols. The use, however, of carboxylic acids avoids this problem since they are of sufficiently low acidity they do not promote over-condensation and it is not necessary to regulate so closely the amount of carboxylic acid used.

The typical phenol or naphthol/formaldehyde-based compounds have the general formula

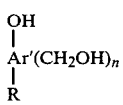

Formula V wherein Ar' is a benzene, naphthalene, X-substituted benzene or X-substituted naphthalene nucleus, n is 1 or 2, and R is a hydrocarbon-based substituent of at least about 30 aliphatic carbon atoms, and X is selected from the group consisting of lower alkyl groups, lower alkoxy groups, lower mercapto groups, fluorine atoms and chlorine atoms. An especially preferred class are those of the general formula

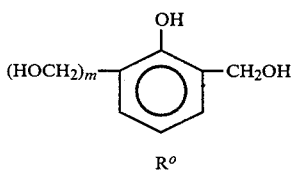

Formula VI wherein $R^o$ is an alkyl substituent of about 30 to about 300 carbon atoms derived from polymerization or interpolymerization of at least one monoolefin of 2 to 10 carbon atoms, and m is 1 or 0.

The polynuclear rings of Ar also may be joined by alkylene linkages such as —$CH_2$—. Such methylol substituted phenolic compounds may be represented by the formula

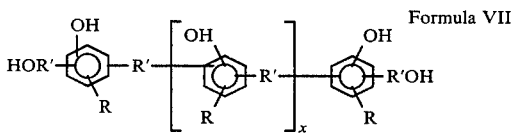

Formula VII wherein each R is substantially saturated hydrocarbon based group of an average of over 10 aliphatic carbon atoms and preferably over 30 carbon atoms up to about 450 carbon atoms, R' is a lower alkylene group of from one to about 7 carbon atoms, and n is an integer from 0 to 20, preferably 0 to 5.

These linked phenolic compounds can be prepared by reacting the alkyl phenols with a slight excess of aldehydes under alkaline conditions to the presence of a hydrocarbon solvent at reflux temperature. Examples of suitable aldehydes include formaldehyde, (formalin or other formaldehyde generating compound), acetaldehyde, propionaldehyde, butyraldehyde, etc. Formaldehyde is preferred.

When the reaction is completed, the alkali can be washed from the hydrocarbon solution of product, and the product recovered by evaporating or distilling the solvent. Unreacted aldehyde also is removed in this step.

The alkylated phenols may be any of the alkylated phenolic compounds described earlier. The preparation of alkylene linked methylol substituted phenols is described in the prior art such as in U.S. Pat. No. 3,737,465, which specification is hereby incorporated by reference for such disclosure.

In another preferred embodiment, the phenols used in the two-cycle oils of this invention contain one each of the foregoing substituents and but a single aromatic ring, most preferably benzene. This preferred class of phenols can be represented by the formula

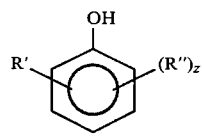

Formula VIII wherein the R' group is a hydrocarbon-based group of about 10 to about 400 aliphatic carbon atoms located ortho or para to the hydroxyl group, R" is a lower alkyl, lower alkoxyl, methylol or lower hydrocarbon based substituted methylol or halogen atom and z is 0 or 1. Usually z is 0 to 2 and R' is a substantially saturated, purely aliphatic group. Often R' is an alkyl or alkenyl group para to the —OH substituent.

In a still more preferred embodiment of this invention, the phenol is of the formula

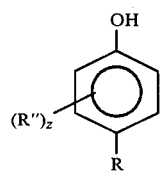

Formula IX wherein R' is derived from homopolymerized or interpolymerized $C_{2-10}$ 1-olefins and has an average of from about 30 to about 300 aliphatic carbon atoms and R" and z are as defined above. Usually R is derived from ethylene, propylene, butylene and mixtures thereof. Typically, it is derived from polymerized isobutene. Often R has at least about 50 aliphatic carbon atoms and z is 0.

The following examples describe exemplary preparations of typical alkyl phenols for use in the two-cycle engine oils of this invention. As will be readily apparent to those skilled in the art, alkyl phenols prepared by other techniques can also be used. All parts and percentages are by weight, and all temperatures are in degrees Celsius, in these examples and elsewhere in this specification unless expressly stated to the contrary.

EXAMPLE A-1

An alkylated phenol is prepared by reacting phenol with polyisobutene having a number average molecular weight of approximately 1000 (vapor phase osmometry) in the presence of a boron trifluoride phenol complex catalyst. Stripping of the product thus formed first to 230° C./760 torr (vapor temperature) and then to 205° C. vapor temperature/50 torr provides purified alkylated phenol.

EXAMPLE A-2

The procedure of Example A-1 is repeated except that the polyisobutene has an average number molecular weight of about 1400.

EXAMPLE A-3

Polyisobutenyl chloride (4885 parts) having a viscosity at 99° C. of 1306 SUS and containing 4.7% chlorine is added to a mixture of 1700 parts phenol, 118 parts of a sulfuric acid-treated clay and 141 parts zinc chloride at 110°–155° C. during a 4-hour period. The mixture is then kept at 155°–185° C. for 3 hours before being filtered through diatomaceous earth. The filtrate is vacuum stripped to 165° C./0.5 torr. The residue is again filtered through diatomaceous earth. The filtrate is a substituted phenol having an OH content of 1.88%.

EXAMPLE A-4

Sodium hydroxide (42 parts of a 20% aqueous sodium hydroxide solution) is added to a mixture of 453 parts of the substituted phenol described in Example A-3 and 450 parts isopropanol at 30° C. over 0.5 hour. Textile spirits (60 parts) and 112 parts of a 37.7% formalin solution are added at 20° C. over a 0.8 hour period and the reaction mixture is held at 4°–25° C. for 92 hours. Additional textile spirits (50 parts), 50 parts isopropanol and acetic acid (58 parts of a 50% aqueous acetic acid solution) are added. The pH of the mixture is 5.5 (as determined by ASTM procedure D-974). The mixture is dried over 20 parts magnesium sulfate and then filtered through diatomaceous earth. The filtrate is vacuum stripped to 25° C./10 torr. The residue is the desired methylol-substituted product having an OH content of 3.29%.

EXAMPLE A-5

Aluminum chloride (76 parts) is slowly added to a mixture of 4220 parts of polyisobutenyl chloride having a number average molecular weight, $\overline{M}n$, of 1000 (VPO) and containing 4.2% chlorine, 1516 parts phenol, and 2500 parts toluene at 60° C. The reaction mixture is kept at 95° C. under a below-the-surface nitrogen gas purge for 1.5 hours. Hydrochloric acid (50 parts of a 37.5% aqueous hydrochloric acid solution) is added at room temperature and the mixture stored for 1.5 hours. The mixture is washed five times with a total of 2500 parts water and then vacuum stripped to 215° C./1 torr. The residue is filtered at 150° C. through diatomaceous earth to improve its clarity. The filtrate is a substituted phenol having an OH content of 1.39%, a Cl content of 0.46% and a $\overline{M}n$ of 898 (VPO).

EXAMPLE A-6

Paraformaldehyde (38 parts) is added to a mixture of 1399 parts of the substituted phenol described in Example A-5, 200 parts toluene, 50 parts water and 2 parts of a 37.5% aqueous hydrochloric acid solution at 50° C. and held for one hour. The mixture is then vacuum stripped to 150° C./15 torr and the residue is filtered through diatomaceous earth. The filtrate is the desired product having an OH content of 1.60%, $\overline{M}n$ of 1688 (GPC) and a weight number average molecular weight, $\overline{M}w$, of 2934 (GPC).

EXAMPLE A-7

There are combined and stirred in a reactor having a reflux condenser 168 grams (0.19 mole) p-polypropyl phenol of 894 $\overline{M}n$ (polypropyl group of about 800 $\overline{M}n$), 31 g. formalin (37% CH$_2$O) to provide 0.38 mole formaldehyde, 100 ml. hexane and 130 ml. of aqueous 1.5N sodium hydroxide. The resulting stirred mixture is heated under reflux (about 70° C.) for about 16 hours. Thereafter, the resulting mixture is washed thoroughly with water to remove the caustic and the hexane is evaporated by heating the water washed solution to about 100° C. The residue, a viscous liquid at ambient temperatures contains the bis-methylol compound of about 4588 $\overline{M}n$ having the structure before indicated wherein x is 4 and each R is polypropyl of about 800 $\overline{M}n$.

EXAMPLE A-8

To a reactor having a stirrer and reflux condenser there are added 1070 grams of 0.5 gram mole p-polypropylphenol of 900 $\overline{M}n$ (polypropyl group of about 803 $\overline{M}n$) dissolved (42%) in a mixture of 10 weight percent polypropylene (803 $\overline{M}n$) and 90 weight percent light mineral oil, 40 grams NaOH and 200 ml. iso-octane. The resulting solution is stirred and heated while 170 g. of formalin (37% CH$_2$O) to provide 2.08 moles formaldehyde are slowly added. The reaction mixture is stirred and heated to 250° F. at which time nitrogen is injected to assist removal of iso-octane. The stirred residue is held at 300° F. for two hours. The liquid residue is filtered to remove solid NaOH. The filtrate is an oil solution of the desired product.

Other examples of alkylated phenols useful in accordance with this invention are shown in Table A.

TABLE A

| Example | Name | Mol. Wt. |
|---|---|---|
| A-9 | 2,2'-dipoly(isobutene)yl-4,4'-dihydroxybiphenyl | 2500 |
| A-10 | 8-hydroxy-poly(propene)yl-1-azanaphthalene | 900 |
| A-11 | 4-poly(isobutene)yl-1-naphthol | 1700 |
| A-12 | 2-poly(propene/butene-1)yl-4,4'-isopropylidene-bisphenol[2] | 3200 |
| A-13 | 4-tetra(propene)yl-2-hydroxyanthracene | — |
| A-14 | 4-octadecyl-1,3-dihydroxybenzene | — |
| A-15 | 4-poly(isobutene)-3-hydroxypyridine | 1300 |

[1]Number average molecular weight by vapor phase osmometry.
[2]The molar ratio of propene to butene-1 in the substituent is 2:3.

In general, the two-cycle engine lubricating oil compositions of this invention contain about 98 to about 55% oil or mixture of oils of lubricating viscosity. Typical compositions contain about 96 to about 70% oil. The presently preferred oils are mineral oils and mineral oil-synthetic polymer and/or ester oil mixtures. Polybutenes of molecular weights of about 250 to about 1,000 (as measured by vapor phase osmometry) and fatty acid ester oils of polyols such as pentaerythritol and trimethylol propane are typical useful synthetic oils.

These oil compositions may contain about 2 to about 30% and typically about 1 to about 20%, of at least one alkyl phenol as described hereinabove. Other additives such as auxiliary detergents and dispersents of the ash-producing or ashless type, anti-oxidants, coupling agents, pour point depressing agents, extreme pressure agents, color stabilizers and anti-foam agents can also be present. In a preferred embodiment detergent/dispersants are present in the lubricating compositions of the invention.

(B) The Detergent/Dispersants

In general the detergent/dispersants (B) which may be used in the lubricants of this invention are materials known to those skilled in the art and they have been described in numerous books, articles and patents. A number of patents are noted hereinbelow in relation to specific types of detergent/dispersants, and where this is done it is to be understood that they are incorporated by reference for their disclosures relevant to the subject matter discussed at the point in the specification in which they are identified.

(B)(i) The Neutral or Basic Metal Salts of Organic Sulfur Acids, Carboxylic Acids or Phenols The choice of metal used to make these salts is usually not critical and therefore virtually any metal can be used. For reasons of availability, cost and maximum effectiveness, certain metals are more commonly used. These include the metals of Groups I, II and III and in particular the alkali and alkaline earth metals (i.e., the Group IA and IIA metals excluding francium and radium). Group IIB metals as well as polyvalent metals such as aluminum, antimony, arsenic, chromium, molybdenum, wolfram, manganese, iron, cobalt, nickel, and copper can also be used. Salts containing a mixture of ions of two or more of these metals are often used.

These salts can be neutral or basic. The former contain an amount of metal cation just sufficient to neutralize the acidic groups present in salt anion; the latter contain an excess of metal cation and are often termed overbased, hyperbased or superbased salts.

These basic and neutral salts can be of oil-soluble organic sulfur acids such as sulfonic, sulfamic, thiosulfonic, sulfinic, partial ester sulfuric, sulfurous and thiosulfuric acid. Generally they are salts of carbocyclic or aliphatic sulfonic acids.

The carbocyclic sulfonic acids include the mono- or poly-nuclear aromatic or cycloaliphatic compounds. The oil-soluble sulfonates can be represented for the most part by the following formulae:

$[R_x-T-(SO_3)_y]_z M_b$   Formula X $[R'-(SO_3)_a]_d M_b$   Formula XI

In the above formulae, M is either a metal cation as described hereinabove or hydrogen; T is a cyclic nucleus such as, for example, benzene, naphthalene, anthracene, phenanthrene, diphenylene oxide, thianthrene, phenothioxine, diphenylene sulfide, phenothiazine, diphenyl oxide, diphenyl sulfide, diphenylamine, cyclohexane, petroleum naphthenes, decahydro-naphthalene, cyclopentane, etc; R in Formula X is an aliphatic group such as alkyl, alkenyl, alkoxy, alkoxyalkyl, carboalkoxyalkyl, etc.; x is at least 1, and $R_x+T$ contains a total of at least about 15 carbon atoms. R' in Formula XI is an aliphatic radical containing at least about 15 carbon atoms and M is either a metal cation or hydrogen. Examples of types of the R' radical are alkyl, alkenyl, alkoxyalkyl, carboalkoxyalkyl, etc. Specific examples of R' are groups derived from petrolatum, saturated and unsaturated paraffin wax, and polyolefins, including polymerized $C_2$, $C_3$, $C_4$, $C_5$, $C_6$, etc., olefins containing from about 15 to 7000 or more carbon atoms. The groups T, R, and R' in the above formulae can also contain other inorganic or organic substituents in addition to those enumerated above such as, for example, hydroxy, mercapto, halogen, nitro, amino, nitroso, sulfide, disulfide, etc. In Formula X, x, y, z and b are at least 1, and likewise in Formula XI, a, b and d are at least 1.

The following are specific examples of oil-soluble sulfonic acids coming within the scope of Formulae X and XI above, and it is to be understood that such examples serve also to illustrate the salts of such sulfonic acids useful in this invention. In other words, for every sulfonic acid enumerated it is intended that the corresponding neutral and basic metal salts thereof are also understood to be illustrated. Such sulfonic acids are mahogany sulfonic acids; bright stock sulfonic acids; sulfonic acids derived from lubricating oil fractions having a Saybolt viscosity from about 100 seconds at 100° F. to about 200 seconds at 210° F.; petrolatum sulfonic acids; mono- and poly-wax substituted sulfonic and polysulfonic acids of, e.g., benzene, naphthalene, phenol, diphenyl ether, naphthalene disulfide, diphenylamine, thiophene, alpha-chloronaphthalene, etc.; other substituted sulfonic acids such as alkyl benzene sulfonic acids (where the alkyl group has at least 8 carbons), cetylphenol mono-sulfide sulfonic acids, dicetyl thianthrene disulfonic acids, dilauryl beta naphthyl sulfonic acids, dicapryl netronaphthalene sulfonic acids, and alkaryl sulfonic acids such as dodecyl benzene "bottoms" sulfonic acids.

The latter are acids derived from benzene which has been alkylated with propylene tetramers or isobutene trimers to introduce 1, 2, 3, or more branched-chain $C_{12}$ substituents on the benzene ring. Dodecyl benzene bottoms, principally mixtures of mono- and di-dodecyl benzenes, are available as by-products from the manufacture of household detergents. Similar products obtained from alkylation bottoms formed during manufacture of linear alkyl sulfonates (LAS) are also useful in making the sulfonates used in this invention.

The production of sulfonates from detergent manufacture by-products by reaction with, e.g., $SO_3$, is well known to those skilled in the art. See, for example, the article "Sulfonates" in Kirk-Othmer "Encyclopedia of Chemical Technology", Second Edition, Vol. 19, pp. 291 et seq. published by John Wiley & Sons, N.Y. (1969).

Other descriptions of neutral and basic sulfonate salts and techniques for making them can be found in the following U.S. Pat. Nos.: 2,174,110, 2,174,506; 2,174,508; 2,193,824; 2,197,800; 2,202,781; 2,212,786; 2,213,360; 2,228,598; 2,223,676; 2,239,974; 2,263,312; 2,276,090; 2,276,097; 2,315,514; 2,319,121; 2,321,022; 2,333,568; 2,333,788; 2,335,259; 2,337,552; 2,347,568, 2,366,027; 2,374,193; 2,383,319; 3,312,618; 3,471,403; 3,488,284; 3,595,790; and 3,798,012. These are hereby incorporated by reference for their disclosures in this regard. Also included are aliphatic sulfonic acids such as paraffin wax sulfonic acids, unsaturated paraffin wax sulfonic acids, hydroxy-substituted paraffin wax sulfonic acids, hexapropylene sulfonic acid, tetra-amylene sulfonic acids, polyisobutene sulfonic acids wherein the polyisobutene contains from 20 to 7000 or more carbon atoms, chloro-substituted paraffin wax sulfonic acids, nitro-paraffin wax sulfonic acids, etc; cycloaliphatic sulfonic acids such as petroleum naphthene sulfonic acids, cetyl cyclopentyl sulfonic acids, lauryl cyclohexyl sulfonic acids, bis(di-isobutyl)cyclohexyl sulfonic acids, mono- or poly-wax substituted cyclohexyl sulfonic acids, etc.

With respect to the sulfonic acids or salts thereof described herein and in the appended claims, it is intended herein to employ the term "petroleum sulfonic acids" or "petroleum sulfonates" to cover all sulfonic acids or the salts thereof derived from petroleum products. A particularly valuable group of petroleum sulfonic acids are the mahogany sulfonic acids (so called because of their reddish-brown color) obtained as a by-product from the manufacture of petroleum white oils by a sulfuric acid process.

Generally Group IA, IIA and IIB neutral and basic salts of the above-described synthetic and petroleum sulfonic acids are useful in the practice of this invention.

The carboxylic acids from which suitable neutral and basic salts for use in this invention can be made include aliphatic, cycloaliphatic, and aromatic mono- and polybasic carboxylic acids such as the naphthenic acids, alkyl- or alkenyl-substituted cyclopentanoic acids, alkyl- or alkenyl-substituted cyclohexanoic acids, alkyl- or alkenyl-substituted aromatic carboxylic acids. The aliphatic acids generally contain at least eight carbon atoms and preferably at least twelve carbon atoms. Usually they have no more than about 400 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acids, alpha-linolenic acid, propylene-tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentane carboxylic acid, myristic acid, dilauryldecahydronaphthalene carboxylic acid, stearyl-octahydroindene carboxylic acid, palmitic acid, commercially available mixtures of two or more carboxylic acids such as tall oil acids, rosin acids, and the like.

A preferred group of oil-soluble carboxylic acids useful in preparing the salts used in the present invention are the oil-soluble aromatic carboxylic acids. These acids are represented by the general formula:

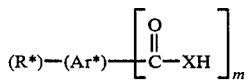

Formula XII where $R^*$ is an aliphatic hydrocarbon-based group of at least four carbon atoms, and no more than about 400 aliphatic carbon atoms, a is an integer of from one to four, $Ar^*$ is a polyvalent aromatic hydrocarbon nucleus of up to about 14 carbon atoms, each X is independently a sulfur or oxygen atoms, and m is an integer of from one to four with the proviso that $R^*$ and a are such that there is an average of at least 8 aliphatic carbon atoms provided by the $R^*$ groups of each acid molecule represented by Formula XII. Examples of aromatic nuclei represented by the variable $Ar^*$ are the polyvalent aromatic radicals derived from benzene, naphthalene, anthracene, phenanthrene, indene, fluorene, biphenyl, and the like. Generally, the radical represented by $Ar^*$ will be a polyvalent nucleus derived from benzene or naphthalene such as phenylenes and naphthylene, e.g., methylphenylenes, ethoxyphenylenes, nitrophenylenes, isopropylphenylenes, hydroxyphenylenes, mercaptophenylenes, N,N-dimethylaminophenylenes, chlorophenylenes, dipropoxynaphthylenes, triethylnaphthylenes, and similar tri-, tetra-, pentavalent nuclei thereof, etc.

The $R^*$ groups are usually purely hydrocarbyl groups, preferably groups such as alkyl or alkenyl radicals. However, the $R^*$ groups can contain small number substituents such as phenyl, cycloalkyl (e.g., cyclohexyl, cyclopentyl, etc.) and nonhydrocarbon groups such as nitro, amino, halo (e.g., chloro, bromo, etc.), lower alkoxy, lower alkyl mercapto, oxo substituents (i.e., =O), thio groups (i.e., =S), interrupting groups such as —NH—, —O—, —S—, and the like provided the essentially hydrocarbon character of the $R^*$ group is retained. The hydrocarbon character is retained for purposes of this invention so long as any non-carbon atoms present in the $R^*$ groups do not account for more than about 10% of the total weight of the $R^*$ groups.

Examples of $R^*$ groups include butyl, isobutyl, pentyl, octyl, nonyl, dodecyl, docosyl, tetracontyl, 5-chlorohexyl, 4-ethoxypentyl, 2-hexenyl, e-cyclohexyloctyl, 4-(p-chlorophenyl)-octyl, 2,3,5-trimethylheptyl, 2-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers, and the like. Likewise, the group Ar may contain non-hydrocarbon substituents, for example, such diverse substituents as lower alkoxy, lower alkyl mercapto, nitro, halo, alkyl or alkenyl groups of less than four carbon atoms, hydroxy, mercapto, and the like.

A group of particularly useful carboxylic acids are those of the formula:

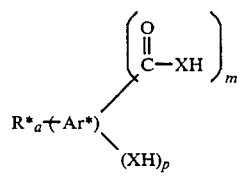

Formula XIII where $R^*$, X, $Ar^*$, m and a are as defined in Formula XIV and p is an integer of 1 to 4, usually 1 or 2. Within this group, an especially preferred class of oil-soluble carboxylic acids are those of the formula:

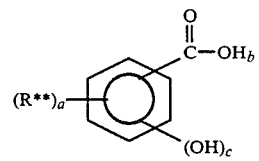

Formula XIV where $R^{}$ in Formula XIV is an aliphatic hydrocarbon group containing at least 4 to about 400 carbon atoms, a is an integer of from 1 to 3, b is 1 or 2, c is zero, 1, or 2 and preferably 1 with the proviso that $R^{}$ and a are such that the acid molecules contain at least an average of about twelve aliphatic carbon atoms in the aliphatic hydrocarbon substituents per acid molecule. And within this latter group of oil-soluble carboxylic acids, the aliphatic-hydrocarbon substituted salicyclic acids wherein each aliphatic hydrocarbon substituent contains an average of at least about sixteen carbon atoms per substituent and one to three substituents per molecule are particularly useful. Salts prepared from such salicyclic acids wherein the aliphatic hydrocarbon substituents are derived from polymerized olefins, particularly polymerized lower 1-mono-olefins such as polyethylene, polypropylene, polyisobutylene, ethylene/propylene copolymers and the like and having average carbon contents of about 30 to 400 carbon atoms.

The carboxylic acids corresponding to Formulae XII and XIII above are well known or can be prepared according to procedures known in the art. Carboxylic acids of the type illustrated by the above formulae and processes for preparing their neutral and basic metal salts are well known and disclosed, for example, in such U.S. Pat. Nos. as 2,197,832; 2,197,835; 2,252,662; 2,252,664; 2,714,092; 3,410,798 and 3,595,791.

Another type of neutral and basic carboxylate salt used in this invention are those derived from alkenyl succinates of the general formula $$R^*-\underset{\underset{CH_2COOH}{|}}{CHCOOH} \qquad \text{Formula XV}$$

wherein R* is as defined above in Formula XII. Such salts and means for making them are set forth in U.S. Pat. Nos. 3,271,130; 3,567,637 and 3,632,610, which are hereby incorporated by reference in this regard.

Other patents specifically describing techniques for making basic salts of the hereinabove-described sulfonic acids, carboxylic acids, and mixtures of any two or more of these include U.S. Pat. Nos. 2,501,731; 2,616,904; 2,616,905; 2,616,906; 2,616,911, 2,616,924; 2,616,925; 2,617,049, 2,777,874; 3,027,325; 3,256,186; 3,282,835; 3,384,585; 3,373,108; 3,368,396; 3,342,733; 3,320,162; 3,312,618; 3,318,809; 3,471,403; 3,488,284; 3,595,790; and 3,629,109. The disclosures of these patents are hereby incorporated in this present specification for their disclosure in this regard as well as for their disclosure of specific suitable basic metal salts.

Neutral and basic salts of phenols (generally known as phenates) are also useful in the compositions of this invention and well known to those skilled in the art. The phenols from which these phenates are formed are of the general formula $$(R^*)_n-(Ar^*)-(XH)_m \qquad \text{Formula XVI}$$

wherein R*, n, Ar*, X and m have the same meaning and preferences as described hereinabove with reference to Formula XII. The same examples described with respect to Formula XII also apply.

The commonly available class of phenates are those made from phenols of the general formula Formula XVII (R')$_a$—⬡—(OH)$_b$
(R$^4$)

wherein a is an integer of 1–3, b is of 1 or 2, z is 0 or 1, R' in Formula XVII is a substantially saturated hydrocarbon-based substituent having an average of from 30 to about 400 aliphatic carbon atoms and R is selected from the group consisting of lower alkyl, lower alkoxyl, nitro, and halo groups.

One particular class of phenates for use in this invention are the basic (i.e., overbased, etc.) Group IIA metal sulfurized phenates made by sulfurizing a phenol as described hereinabove with a sulfurizing agent such as sulfur, a sulfur halide, or sulfide or hydrosulfide salt. Techniques for making these sulfurized phenates are described in U.S. Pat. Nos. 2,680,096; 3,036,971 and 3,775,321 which are hereby incorporated by reference for their disclosures in this regard.

Other phenates that are useful are those that are made from phenols that have been linked through alkylene (e.g., methylene) bridges. These are made by reacting single or multi-ring phenols with aldehydes or ketones, typically, in the presence of an acid or basic catalyst.

Such linked phenates as well as sulfurized phenates are described in detail in U.S. Pat. No. 3,350,038; particularly columns 6–8 thereof, which is hereby incorporated by reference for its disclosures in this regard.

Naturally, mixtures of two or more neutral and basic salts of the hereinabove described organic sulfur acids, carboxylic acids and phenols can be used in the compositions of this invention. Usually the neutral and basic salts will be sodium, lithium, magnesium, calcium, or barium salts including mixtures of two or more of any of these.

(B)(ii) The Hydrocarbyl-Substituted Amine

The hydrocarbyl-substituted amines used in making the compositions of this invention are well known to those of skill in the art and they are described in a number of patents. Among these are U.S. Pat. Nos. 3,275,554; 3,438,757; 3,454,555; 3,565,804; 3,755,433; and 3,822,209. These patents are hereby incorporated by their reference for their disclosure of suitable hydrocarbyl amines for use in the present invention including their method of preparation.

A typical hydrocarbyl amine has the general formula:

$$([AXN]_x[-N([-UN-]_a[-UN \underset{\underset{}{\diagdown\_\diagup}}{\overset{\diagup\overline{\phantom{SS}}\diagdown}{S}} N-]_b)]_y R^2_c H_{1+2y+ay-c} \qquad \text{Formula XVIII}$$

wherein A is hydrogen, a hydrocarbyl group of from 1 to 10 carbon atoms, or hydroxyhydrocarbyl group of from 1 to 10 carbon atoms; X is hydrogen, a hydrocarbyl group of from 1 to 10 carbon atoms, or hydroxyhydrocarbyl group of from 1 to 10 carbon atoms, and may be taken together with A and N to form a ring of from 5 to 6 annular members and up to 12 carbon atoms; U is an alkylene group of from 2 to 10 carbon atoms, $R^2$ is an aliphatic hydrocarbon of from about 30 to 400 carbon atoms; a is an integer of from 0 to 10; b is an integer of from 0 to 1; a+2b is an integer of from 1 to 10; c is an integer of from 1 to 5 and is as an average in the range of 1 to 4, and equal to or less than the number of nitrogen atoms in the molecule; x is an integer of from 0 to 1; y is an integer of from 0 to 1; and x+y is equal to 1.

In interpreting this formula, it is to be understood that the $R^2$ and H atoms are attached to the unsatisfied nitrogen valences within the brackets of the formula. Thus, for example, the formula includes subgeneric formulae wherein the $R^2$ is attached to terminal nitrogens and isomeric subgeneric formula wherein it is attached to non-terminal nitrogen atoms. Nitrogen atoms not attached to an $R^2$ may bear a hydrogen or an AXN substituent.

The hydrocarbyl amines useful in this invention and embraced by the above formula include monoamines of the general formula $$AXNR^2 \qquad \text{Formula XIX}$$

Illustrative of such monoamines are the following:
poly(propylene)amine
N,N-dimethyl-N-poly(ethylene/propylene)amine
   (50:50 mole ratio of monomers)
poly(isobutene)amine N,N-di(hydroxyethyl)-N-poly(isobutene)amine
poly(isobutene/1-butene/2-butene)amine (50:25:25 mole ratio of monomer)
N-(2-hydroxypropyl)-N-poly(isobutene)amine
N-poly(1-butene)-aniline
N-poly(isobutene)-morpholine Among the hydrocarbyl amines embraced by the general Formula XVII as set forth above, are polyamines of the general formula

   Formula XX

Illustrative of such polyamines are the following:
N-poly(isobutene)ethylene diamine
N-poly(propylene)trimethylene diamine
N-poly(1-butene)diethylene triamine
N',N'-poly(isobutene)tetraethylene pentamine
N,N-dimethyl-N'-poly(propylene), 1,3-propylene diamine The hydrocarbyl substituted amines useful in forming the compositions of this invention include certain N-amino-hydrocarbyl morpholines which are not embraced in the general Formula XVIII above. These hydrocarbyl-substituted aminohydrocarbyl morpholines have the general formula:

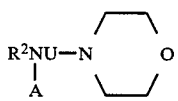   Formula XXI wherein $R^2$ is an aliphatic hydrocarbon group of from about 30 to about 400 carbons, A is hydrogen, hydrocarbyl of from 1 to 10 carbon atoms or hydroxy hydrocarbyl group of from 1 to 10 carbon atoms and U is an alkylene group of from 2 to 10 carbon atoms. These hydrocarbyl-substituted aminohydrocarbyl morpholines as well as the polyamines described by Formula XIX are among the typical hydrocarbyl-substituted amines used in preparing compositions of this invention.

(B)(iii) The acylated Nitrogen-Containing Compounds

A number of acylated, nitrogen-containing compounds having a substituent of at least 10 aliphatic carbon atoms and made by reacting a carboxylic acid acylating agent with an amino compound are known to those skilled in the art. In such compositions the acylating agent is linked to the amino compound through an imido, amido, amidine or acyloxy ammonium linkage. The substituent of 10 aliphatic carbon atoms may be in either the carboxylic acid acylating agent derived portion of the molecule or in the amino compound derived portion of the molecule. Preferably, however, it is in the acylating agent portion. The acylating agent can vary from formic acid and its acylating derivatives to acylating agents having high molecular weight aliphatic substituents of up to 5,000, 10,000 or 20,000 carbon atoms. The amino compounds can vary from ammonia itself to amines having aliphatic substituents of up to about 30 carbon atoms.

A typical class of acylated amino compounds useful in making the compositions of this invention are those made by reacting an acylating agent having an aliphatic substituent of at least 10 carbon atoms and a nitrogen compound characterized by the presence of at least one —NH group. Typically, the acylating agent will be a mono- or polycarboxylic acid (or reactive equivalent thereof) such as a substituted succinic or propionic acid and the amino compound will be a polyamine or mixture of polyamines, most typically, a mixture of ethylene polyamines. The aliphatic substituent in such acylating agents is often of at least about 50 and up to about 400 carbon atoms. Usually it belongs to the same generic class as the R' group of the phenols (A) and therefore the preferences, examples and limitation discussed hereinabove relating to R' apply equally to this aliphatic substituent. Exemplary of amino compounds useful in making these acylated compounds are the following:

(1) polyalkylene polyamines of the general formula

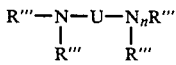   Formula XXII wherein each R''' is independently a hydrogen atom or a $C_{1-12}$ hydrocarbon-based group, with proviso that at least one R is a hydrogen atom, n is a whole number of 1 to 10 and U is a $C_{2-10}$ alkylene group, (2) heterocyclic-substituted polyamines of the formula

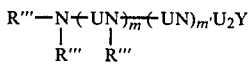   Formula XXIII wherein R''' and U are as defined hereinabove, m is 0 or a whole number of 1 to 10, m' is a whole number of 1 to 10 and Y is oxygen or divalent sulfur atom or a N—R''' group and (3) aromatic polyamines of the general formula

   Formula XXIV wherein Ar is an aromatic nucleus of 6 to about 20 carbon atoms, each R''' is as defined hereinabove and y is 2 to about 8. Specific examples of the polyalkylene polyamines (1) are ethylene diamine, tetra(ethylene)-pentamine, tri-(trimethylene)tetramine, 1,2-propylene diamine, etc. Specific examples of the heterocyclic-substituted polyamines (2) are N-2-aminoethyl piperazine, N-2 and N-3 amino propyl morpholine, N-3-(dimethyl amino)propyl piperazine, etc. Specific examples of the aromatic polyamines (3) are the various isomeric phenylene diamines, the various isomeric naphthalene diamines, etc.

Many patents have described useful acylated nitrogen compounds including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; and 3,804,763. A typical acylated nitrogen-containing compound of this class is that made by reacting a poly(isobutene)-substituted succinic anhydride acylating agent (e.g., anhydride, acid, ester, etc.) wherein the poly(isobutene) substituent has between about 50 to about 400 carbon atoms with a mixture of ethylene polyamines having 3 to about 7 amino nitrogen atoms per ethylene polyamine and about 1 to about 6 ethylene units made from condensation of ammonia with ethylene chloride. In view of the extensive disclosure of this type of acylated amino compound, further discussion of their nature and method of preparation is not needed here. Instead, the above-noted U.S. Patents are hereby incorporated by reference for their disclosure of acylated amino compounds and their method of preparation.

Another type of acylated nitrogen compound belonging to this class is that made by reacting the afore-described alkylene amines with the afore-described substituted succinic acids or anhydrides and aliphatic monocarboxylic acids having from 2 to about 22 carbon atoms. In these types of acylated nitrogen compounds, the mole ratio of succinic acid to monocarboxylic acid ranges from about 1:0.1 to about 1:1. Typical of the monocarboxylic acid are formic acid, acetic acid, dodecanoic acid, butanoic acid, oleic acid, stearic acid, the commercial mixture of stearic acid isomers known as isostearic acid, tolyl acid, etc. Such materials are more fully described in U.S. Pat. Nos. 3,216,936 and 3,250,715 which are hereby incorporated by reference for their disclosures in this regard.

Still another type of acylated nitrogen compound useful in making the compositions of this invention is the product of the reaction of a fatty monocarboxylic acid of about 12–30 carbon atoms and the aforedescribed alkylene amines, typically, ethylene, propylene or trimethylene polyamines containing 2 to 8 amino groups and mixtures thereof. The fatty monocarboxylic acids are generally mixtures of straight and branched chain fatty carboxylic acids containing 12–30 carbon atoms. A widely used type of acylated nitrogen compound is made by reacting the afore-described alkylene polyamines with a mixture of fatty acids having from 5 to about 30 mole percent straight chain acid and about 70 to about 95 percent mole branched chain fatty acids. Among the commercially available mixtures are those known widely in the trade as isostearic acid. These mixtures are produced as a by-product from the dimerization of unsaturated fatty acids as described in U.S. Pat. Nos. 2,812,342 and 3,260,671.

The branched chain fatty acids can also include those in which the branch is not alkyl in nature, such as found in phenyl and cyclohexyl stearic acid and the chlorostearic acids. Branched chain fatty carboxylic acid/alkylene polyamine products have been described extensively in the art. See for example, U.S. Pat. Nos. 3,110,673; 3,251,853; 3,326,801; 3,337,459; 3,405,064; 3,429,674; 3,468,639; 3,857,791. These patents are hereby incorporated by reference for their disclosure of fatty acid/polyamine condensates for their use in lubricating oil formulations.

(B)(iv) The Nitrogen-containing Condensates of Phenols, Aldehydes, and Amino Compounds The phenol/aldehyde/amino compound condensates useful in making the detergent/dispersants of this invention include those generically referred to as Mannich condensates. Generally they are made by reacting simultaneously or sequentially at least one active hydrogen compound such as a hydrocarbon-substituted phenol (e.g., and alkyl phenol wherein the alkyl group has at least about 30 up to about 400 carbon atoms), having at least one hydrogen atom bonded to an aromatic carbon, with at least one aldehyde or aldehyde-producing material (typically formaldehyde or formaldehyde precursor) and at least one amino or polyamino compound having at least one NH group. The amino compounds include primary or secondary monoamines having hydrocarbon substituents of 1 to 30 carbon atoms or hydroxyl-substituted hydrocarbon substituents of 1 to about 30 carbon atoms. Another type of typical amino compound are the polyamines described during the discussion of the acylated nitrogen-containing compounds.

Exemplary mono-amines include methyl ethyl amine, methyl octadecyl amine, aniline, diethyl amine, diethanol amine, dipropyl amine and so forth. The following U.S. Patents contain extensive descriptions of Mannich condensates which can be used in making the compositions of this invention:

| U.S. PAT. Nos. | | |
| --- | --- | --- |
| 2,459,112 | 3,413,347 | 3,558,743 |
| 2,962,442 | 3,442,808 | 3,586,629 |
| 2,984,550 | 3,448,047 | 3,591,598 |
| 3,036,003 | 3,454,497 | 3,600,372 |
| 3,166,516 | 3,459,661 | 3,634,515 |
| 3,236,770 | 3,461,172 | 3,649,229 |
| 3,355,270 | 3,493,520 | 3,697,574 |
| 3,368,972 | 3,539,633 | |

These patents are hereby incorporated by reference for their disclosures relating to the production and use of Mannich condensate products in lubricant compositions.

Condensates made from sulfur-containing reactants also can be used in the compositions of the present invention. Such sulfur-containing condensates are described in U.S. Pat. Nos. 3,368,972; 3,649,229; 3,600,372; 3,649,659; and 3,741,896. These patents are also incorporated by reference for their disclosure of sulfur-containing Mannich condensates. Generally the condensates used in making compositions of this invention are made from a phenol bearing an alkyl substituent of about 6 to about 400 carbon atoms, more typically, 30 to about 250 carbon atoms. These typical condensates are made from formaldehyde or $C_{2-7}$ aliphatic aldehyde and an amino compound such as those used in making the acylated nitrogen-containing compounds described under (B)(iii).

These preferred condensates are prepared by reacting about one molar portion of phenolic compound with about 1 to about 2 molar portions of aldehyde and about 1 to about 5 equivalent portions of amino compound (an equivalent of amino compound is its molecular weight divided by the number of =NH groups present). The conditions under which such condensation reactions are carried out are well known to those skilled in the art as evidenced by the above-noted patents. Therefore, these patents are also incorporated by reference for their disclosures relating to reaction conditions.

A particularly preferred class of condensation products for use in the present invention are those made by a "2-step process" as disclosed in commonly assigned U.S. Ser. No. 451,644, filed Mar. 15, 1974 now abandoned. Briefly, these nitrogen-containing condensates are made by (1) reacting at least one hydroxy aromatic compound containing an aliphatic-based or cycloaliphatic-based substituent which has at least about 30 carbon atoms and up to about 400 carbon atoms with a lower aliphatic $C_{k-7}$ aldehyde or reversible polymer thereof in the presence of an alkaline reagent, such as an alkali metal hydroxide, at a temperature up to about 150° C.; (2) substantially neutralizing the intermediate reaction mixture thus formed; and (3) reacting the neutralized intermediate with at least one compound which contains an amino group having at least one —NH— group.

More preferably, these 2-step condensates are made from (a) phenols bearing a hydrocarbon-based substituent having about 30 to about 250 carbon atoms, said substituent being derived from a polymer of propylene, 1-butene, 2-butene, or isobutene and (b) formaldehyde, or reversible polymer thereof, (e.g., trioxane, paraformaldehyde) or functional equivalent thereof, (e.g., methylol) and (c) an alkylene polyamine such as ethylene polyamines having between 2 and 10 nitrogen atoms. Further details as to this preferred class of condensates can be found in the hereinabove noted U.S. Ser. No. 451,644, which is hereby incorporated by reference, for its disclosures relating to 2-step condensates.

(B)(v) The Esters of Substituted Polycarboxylic Acids

The ester useful as detergents/dispersants in this invention are derivatives of substituted carboxylic acids in which the substituent is a substantially aliphatic, substantially saturated hydrocarbon-based radical containing at least about 30 (preferably about 50 to about 750) aliphatic carbon atoms. As used herein, the term "hydrocarbon-based radical" denotes a radical having a carbon atom directly attached to the remainder of the molecule and having predominantly hydrocarbon character within the context of this invention. Such radicals include the following:

(1) Hydrocarbon radicals; that is, aliphatic radicals, aromatic- and alicyclic-substituted aliphatic radicals, and the like, of the type known to those skilled in the art.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are halo, nitro, hydroxy, alkoxy, carbalkoxy and alkylthio.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

The substituted carboxylic acids (and derivatives thereof including esters, amides and imides) are normally prepared by the alkylation of an unsaturated acid, or a derivative thereof such as an anhydride, ester, amide or imide, with a source of the desired hydrocarbon-based radical. Suitable unsaturated acids and derivatives thereof include acrylic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid and 2-pentene-1,3,5-tricarboxylic acid. Particularly preferred are the unsaturated dicarboxylic acids and their derivatives, especially maleic acid, fumaric acid and maleic anhydride.

Suitable alkylating agents include homopolymers and interpolymers of polymerizable olefin monomers containing from about 2 to about 10 and usually from about 2 to about 6 carbon atoms, and polar substituent-containing derivatives thereof. Such polymers are substantially saturated (i.e., they contain no more than about 5% olefinic linkages) and substantially aliphatic (i.e., they contain at least about 80% and preferably at least about 95% by weight of units derived from aliphatic monoolefins). Illustrative monomers which may be used to produce such polymers are ethylene, propylene, 1-butene, 2-butene, isobutene, 1-octene and 1-decene. Any unsaturated units may be derived from conjugated dienes such as 1,3-butadiene and isoprene; non-conjugated dienes such as 1,4-hexadiene, 1,4-cyclohexadiene, 5-ethylidene-2-norbornene and 1,6-octadiene; and trienes such as 1-isopropylidene-3a,4,7,-7a-tetrahydroindene, 1-isopropylidenedicyclopentadiene and 2-(2-methylene-4-methyl-3-pentenyl) [2.2.1]bicyclo-5-heptene.

A first preferred class of polymers comprises those of terminal olefins such as propylene, 1-butene, isobutene and 1-hexene. Especially preferred within this class are polybutenes comprising predominantly isobutene units. A second preferred class comprises terpolymers of ethylene, a $C_{3-8}$ alpha-monoolefin and a polyene selected from the group consisting of non-conjugated dienes (which are especially preferred) and trienes. Illustrative of these terpolymers is "Ortholeum 2052" manufactured by E. I. duPont de Nemours & Company, which is a terpolymer containing about 48 mole percent ethylene groups, 48 mole percent propylene groups and 4 mole percent 1,4-hexadiene groups and having an inherent viscosity of 1.35 (8.2 grams of polymer in 100 ml. of carbon tetrachloride at 30° C.).

Methods for the preparation of the substituted carboxylic acids and derivatives thereof are well known in the art and need not be described in detail. Reference is made, for example, to U.S. Pat. Nos. 3,272,746; 3,522,179; and 4,234,435, which are incorporated by reference herein. The mole ratio of the polymer to the unsaturated acid or derivative thereof may be equal to, greater than or less than 1, depending on the type of product desired.

When the unsaturated acid or derivative thereof is maleic acid, fumaric acid or maleic anhydride, the alkylation product is a substituted succinic acid or derivative thereof. These substituted succinic acids and derivatives are particularly preferred for preparing the compositions of this invention.

The esters are those of the above-described succinic acids with hydroxy compounds which may be aliphatic compounds such as monohydric and polyhydric alcohols or aromatic compounds such as phenols and naphthols. The aromatic hydroxy compounds from which the esters of this invention may be derived are illustrated by the following specific examples: phenol, beta-naphthol, alpha-naphthol, cresol, resorcinol, catechol, p,p'dihydroxybiphenyl, 2-chlorophenol, 2,4-dibutylphenol, propene tetramer-substituted phenol, didodecylphenol, 4,4'-methylene-bis-phenol, alpha-decyl-beta-naphthol, polyisobutene(molecular weight of 1000)-substituted phenol, the condensation product of heptylphenol with 0.5 mole of formaldehyde, the condensation product of octylphenol with acetone, di(hydroxyphenyl)oxide, di(hydroxyphenyl)sulfide, di(hydroxyphenyl)disulfide, and 4-cyclohexylphenol. Phenol and alkylated phenols having up to three alkyl substituents are preferred. Each of the alkyl substituents may contain 100 or more carbon atoms.

The alcohols from which the esters may be derived preferably contain up to about 40 aliphatic carbon atoms. They may be monohydric alcohols such as methanols, ethanol, isooctanol, dodecanol, cyclohexanol, cyclopentanol, behenyl alcohol, hexatriacontanol, neopentyl alcohol, isobutyl alcohol, benzyl alcohol, beta-phenylethyl alcohol, 2-methylcyclohexanol, beta-chloroethanol, monomethyl ether of ethylene glycol, monobutyl ether of ethylene glycol, monopropyl ether of diethylene glycol, monododecyl ether of triethylene glycol, mono-oleate of ethylene glycol, monostearate of diethylene glycol, sec-pentyl alcohol, tert-butyl alcohol, 5-bromo-dodecanol, nitro-octadecanol and dioleate of glycerol. The polyhydric alcohols preferably contain from 2 to about 10 hydroxy radicals. They are illustrated by, for example, ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols include glycerol, mono-oleate of glycerol, mono-stearate of glycerol, monomethyl ether of glycerol, pentaerythritol, 9,10-dihydroxy stearic acid, methyl ester of 9,10-dihydroxy stearic acid, 1,2-butanediol, 2,3-hexanediol, 2,4-hexanediol, pinacol, erythritol, arabitol, sorbitol, mannitol, 1,2-cyclohexanediol, and xylene glycol. Carbohydrates such as sugars, starches, celluloses, etc., likewise may yield the esters of this invention. The carbohydrates may be exemplified by a glucose, fructose, sucrose, rhamnose, mannose, glyceraldehyde, and galactose.

An especially preferred class of polyhydric alcohols are those having at least three hydroxy radicals, some of which have been esterified with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the mono-oleate of sorbitol, distearate of sorbitol, mono-oleate of glycerol, monostearate of glycerol, di-dodecanoate of erythritol.

The esters may also be derived from unsaturated alcohols such as allyl alcohol, cinnamyl alcohol, propargyl alcohol, 1-cyclohexene-3-ol, an oleyl alcohol. Still other classes of the alcohols capable of yielding the esters of this invention comprise the ether-alcohols and amino-alcohols including, for example, the oxyalkylene-, oxy-arylene-, amino-alkylene-, and amino-arylene-substituted alcohols having one or more oxy-alkylene, amino-alkylene or amino-arylene oxy-arylene radicals. They are exemplified by Cellosolve, carbitol, phenoxyethanol, heptylphenyl-(oxypropylene)$_6$-H, octyl-(oxyethylene)$_{30}$-H, phenyl-(oxyoctylene)$_2$-H, mono(heptylphenyloxypropylene)-substituted glycerol, poly(styrene oxide), amino-ethanol, 3-amino ethyl-pentanol, di(hydroxyethyl)amine, p-aminophenol, tri(hydroxypropyl)amine, N-hydroxyethyl ethylene diamine, N,N,N',N'-tetrahydroxytrimethylene diamine, and the like. For the most part, the ether-alcohols having up to about 150 oxy-alkylene radicals in which the alkylene radical contains from 1 to about 8 carbon atoms are preferred.

The esters may be di-esters of succinic acids or acidic esters, i.e., partially esterified succinic acids; as well as partially esterified polyhydric alcohols or phenols, i.e., esters having free alcoholic or phenolic hydroxyl radicals. Mixtures of the above-illustrated esters likewise are contemplated within the scope of the invention.

The esters may be prepared by one of several methods. The method which is preferred because of convenience and superior properties of the esters it produces, involves the reaction of a suitable alcohol or phenol with a substantially hydrocarbon-substituted succinic anhydride. The esterification is usually carried out at a temperature above about 100° C., preferably between 150° C. and 300° C.

The water formed as a by-product is removed by distillation as the esterification proceeds. A solvent may be used in the esterification to facilitate mixing and temperature control. It also facilitates the removal of water from the reaction mixture. The useful solvents include xylene, toluene, diphenyl ether, chlorobenzene, and mineral oil.

A modification of the above process involves the replacement of the substituted succinic anhydride with the corresponding succinic acid. However, succinic acids readily undergo dehydration at temperatures above about 100° C. and are thus converted to their anhydrides which are then esterified by the reaction with the alcohol reactant. In this regard, succinic acids appear to be the substantial equivalent of their anhydrides in the process.

The relative proportions of the succinic reactant and the hydroxy reactant which are to be used depend to a large measure upon the type of the product desired and the number of hydroxyl groups present in the molecule of the hydroxy reactant. For instance, the formation of a half ester of a succinic acid, i.e., one in which only one of the two acid radicals is esterified, involves the use of one mole of a monohydric alcohol for each mole of the substituted succinic acid reactant, whereas the formation of a diester of a succinic acid involves the use of two moles of the alcohol for each mole of the acid. On the other hand, one mole of a hexahydric alcohol may combine with as many as six moles of a succinic acid to form an ester in which each of the six hydroxyl radicals of the alcohol is esterified with one of the two acid radicals of the succinic acid. Thus, the maximum proportion of the succinic acid to be used with a polyhydric alcohol is determined by the number of hydroxyl groups present in the molecule of the hydroxy reactant. For the purposes of this invention, it has been found that esters obtained by the reaction of equi-molar amounts of the succinic acid reactant and hydroxy reactant have superior properties and are therefore preferred.

In some instances it is advantageous to carry out the esterification in the presence of a catalyst such as sulfuric acid, pyridine hydrochloride, hydrochloric acid, benzene sulfonic acid, p-toluene sulfonic acid, phosphoric acid, or any other known esterification catalyst. The amount of the catalyst in the reaction may be as little as 0.01% (by weight of the reaction mixture), more often from about 0.1% to about 5%.

The esters of this invention likewise may be obtained by the reaction of a substituted succinic acid or anhydride with an epoxide or a mixture of an epoxide and water. Such reaction is similar to one involving the acid or anhydride with a glycol. For instance, the product may be prepared by the reaction of a substituted succinic acid with one mole of ethylene oxide. Similarly, the product may be obtained by the reaction of a substituted succinic acid with two moles of ethylene oxide. Other epoxides which are commonly available for use in such reaction include, for example, propylene oxide, styrene oxide, 1,2-butylene oxide, 2,3-butylene oxide, epichlorohydrin, cyclohexene oxide, 1,2-octylene oxide, epoxidized soya bean oil, methyl ester of 9,10-epoxy-stearic acid, and butadiene mono-epoxide. For the most part, the epoxides are the alkylene oxides in which the alkylene radical has from 2 to about 8 carbon atoms; or the epoxidized fatty acid esters in which the fatty acid radical has up to about 30 carbon atoms and the ester radical is derived from a lower alcohol having up to about 8 carbon atoms.

In lieu of the succinic acid or anhydride, a substituted succinic acid halide may be used in the processes illustrated above for preparing the esters of this invention. Such acid halides may be acid dibromides, acid dichlorides, acid monochlorides, and acid monobromides. The substituted succinic anhydrides and acids can be prepared by, for example, the reaction of maleic anhydride with a high molecular weight olefin or a halogenated hydrocarbon such as is obtained by the chlorination of an olefin polymer described previously. The reaction involves merely heating the reactants at a temperature preferably from about 100° C. to about 250° C. The product from such a reaction is an alkenyl succinic anhydride. The alkenyl group may be hydrogenated to an alkyl group. The anhydride may be hydrolyzed by treatment with water or steam to the corresponding acid. Another method useful for preparing the succinic acids or anhydrides involves the reaction of itaconic acid or anhydride with an olefin or a chlorinated hydrocarbon at a temperature usually within the range from about 100° C. to about 250° C. The succinic acid halides can be prepared by the reaction of the acids or their anhydrides with a halogenation agent such as phosphorus tribromide, phosphorus pentachloride, or thionyl chloride. These and other methods of preparing the succinic compounds are well known in the art and need not be illustrated in further detail here.

Still other methods of preparing the esters of this invention are available. For instance, the esters may be obtained by the reaction of maleic acid or anhydride with an alcohol such as is illustrated above to form a mono- or di-ester of maleic acid and then the reaction of this ester with an olefin or a chlorinated hydrocarbon such as is illustrated above. They may also be obtained by first esterifying itaconic anhydride or acid and subsequently reacting the ester intermediate with an olefin or a chlorinated hydrocarbon under conditions similar to those described hereinabove.

The following specific illustrative examples describe the preparation of exemplary detergent/dispersants useful in the compositions of this invention.

EXAMPLE B-1

A mixture of 906 parts of an oil solution of an alkyl phenyl sulfonic acid (having an average molecular weight of 450, vapor phase osmometry), 564 parts mineral oil, 600 parts toluene, 98.7 parts magnesium oxide and 120 parts water is blown with carbon dioxide at a temperature of 78°–85° C. for seven hours at a rate of about 3 cubic feet of carbon dioxide per hour. The reaction mixture is constantly agitated throughout the carbonation. After carbonation, the reaction mixture is stripped to 165° C./20 torr and the residue filtered. The filtrate is an oil solution of the desired overbased magnesium sulfonate having a metal ratio of about 3.

EXAMPLE B-2

A mixture of 323 parts of mineral oil, 4.8 parts of water, 0.74 parts of calcium chloride, 79 parts of lime, and 128 parts of methyl alcohol is prepared, and warmed to a temperature of about 50° C. To this mixture there is added 1000 parts of an alkyl phenyl sulfonic acid having an average molecular weight (vapor phase osmometry) of 500 with mixing. The mixture then is blown with carbon dioxide at a temperature of about 50° C. at the rate of about 5.4 lbs. per hour for about 2.5 hours. After carbonation, 102 additional parts of oil are added and the mixture is stripped of volatile materials at a temperature of about 150°–155° C. at 50 mm. pressure. The residue is filtered and the filtrate is the desired oil solution of the overbased calcium sulfonate having calcium content of about 3.7% and a metal ratio of about 1.7.

EXAMPLE B-3

A polyisobutenyl succinic anhydride is prepared by reacting a chlorinated poly(isobutene) (having an average chlorine content of 4.3% and an average of 82 carbon atoms) with maleic anhydride at about 200° C. The resulting polyisobutenyl succinic anhydride has a saponification number of 90. To a mixture of 1,246 parts of this succinic anhydride and 100 parts of toluene there is added at 25° C. 76.7 parts of barium oxide. The mixture is heated to 115° C. and 125 parts of water is added drop-wise over a period of one hour. The mixture is then allowed to reflux at 150° C. until all the barium oxide is reacted. Stripping and filtration provides a filtrate having a barium content of 4.71%.

EXAMPLE B-4

A mixture of 1500 parts of chlorinated poly(isobutene) (of molecular weight of about 950 and having a chlorine content of 5.6%), 285 parts of an alkylene polyamine having an average composition corresponding stoichiometrically to tetraethylene pentamine and 1200 parts of benzene is heated to reflux. The mixture's temperature is then slowly increased over a 4-hour period to 170° C. while benzene is removed. The cooled mixture is diluted with an equal volume of mixed hexanes and absolute ethanol (1:1). This mixure is heated to reflux and a ⅓ volume of 10% aqueous sodium carbonate is added to it. After stirring, the mixture is allowed to cool and the phases separate. The organic phase is washed with water and stripped to provide the desired polyisobutenyl polyamine having a nitrogen content of 4.5%.

EXAMPLE B-5

A mixture of 140 parts of toluene and 400 parts of a polyisobutenyl succinic anhydride (prepared from the poly(isobutene) having a molecular weight of about 850, vapor phase osmometry) having a saponification number 109, and 63.6 parts of an ethylene amine mixture having an average composition corresponding in stoichiometry to tetraethylene pentamine, is heated to 150° C. while the water/toluene azeotrope is removed. The reaction mixture is then heated to 150° C. under reduced pressure until toluene ceases to distill. The residual acylated polyamine has a nitrogen content of 4.7%.

EXAMPLE B-6

To 1,133 parts of commercial diethylene triamine heated at 110°–150° C. is slowly added 6820 parts of isostearic acid over a period of two hours. The mixture is held at 150° C. for one hour and then heated to 180° C. over an additional hour. Finally, the mixture is heated to 205° C. over 0.5 hour; throughout this heating, the mixture is blown with nitrogen to remove volatiles. The mixture is held at 205°–230° C. for a total of 11.5 hours and then stripped at 230° C./20 torr to provide the desired acylated polyamine as a residue containing 6.2% nitrogen.

EXAMPLE B-7

To a mixture of 50 parts of a polypropyl-substituted phenol (having a molecular weight of about 900, vapor phase osmometry), 500 parts of mineral oil (a solvent refined paraffinic oil having a viscosity of 100 SUS at 100° F.) and 130 parts of 9.5% aqueous dimethylamine solution (equivalent to 12 parts amine) is added dropwise, over an hour, 22 parts of a 37% aqueous solution of formaldehyde (corresponding to 8 parts aldehyde). During the addition, the reaction temperature is slowly increased to 100° C. and held at that point for three hours while the mixture is blown with nitrogen. To the cooled reaction mixture is added 100 parts toluene and 50 parts mixed butyl alcohols. The organic phase is washed three times with water until neutral to litmus paper and the organic phase filtered and stripped to 200° C./5–10 torr. The residue is an oil solution of the final product containing 0.45% nitrogen.

EXAMPLE B-8

A mixture of 140 parts of a mineral oil, 174 parts of a poly(isobutene) (molecular weight 1000)-substituted succinic anhydride having a saponification number of 105 and 23 parts of isostearic acid is prepared at 90° C. To this mixture there is added 17.6 parts of a mixture of polyalkylene amines having an overall composition corresponding to that of tetraethylene pentamine at 80°–100° C. throughout a period of 1.3 hours. The reaction is exothermic. The mixture is blown at 225° C. with nitrogen at a rate of 5 pounds per hour for 3 hours whereupon 47 parts of an aqueous distillate is obtained. The mixture is dried at 225° C. for 1 hour, cooled to 100° C. and filtered to provide the desired final product in oil solution.

EXAMPLE B-9

A substantially hydrocarbon-substituted succinic anhydride is prepared by chlorinating a polyisobutene having a molecular weight of 1000 to a chlorine content of 4.5% and then heating the chlorinated polyisobutene with 1.2 molar proportions of maleic anhydride at a temperature of 150°–220° C. The succinic anhydride thus obtained has an acid number of 130. A mixture of 874 grams (1 mole) of the succinic anhydride and 104 grams (1 mole) of neopentyl glycol is mixed at 240°–250° C./30 mm. for 12 hours. The residue is a mixture of the esters resulting from the esterification of one and both hydroxy radicals of the glycol. It has a saponification number of 101 and an alcoholic hydroxyl content of 0.2%.

EXAMPLE B-10

The di-methyl ester of the substantially hydrocarbon-substituted succinic anhydride of Example 1 is prepared by heating a mixture of 2185 grams of the anhydride, 480 grams of methanol, and 1000 cc. of toluene at 50°–65° C. while hydrogen chloride is bubbled through the reaction mixture for 3 hours. The mixture is then heated at 60°–65° C. for 2 hours, dissolved in benzene, washed with water, dried and filtered. The filtrate is heated at 150° C./60 mm. to rid it of volatile components. The residue is the defined dimethyl ester.

EXAMPLE B-11

A carboxylic acid ester is prepared by slowly adding 3240 parts of a high molecular weight carboxylic acid (prepared by reacting chlorinated polyisobutylene and acrylic acid in a 1:1 equivalent ratio and having an average molecular weight of 982) to a mixture of 200 parts of sorbitol and 1000 parts of diluent oil over a 1.5-hour period while maintaining a temperature of 115°–125° C. Then 400 parts of additional diluent oil are added and the mixture is maintained at about 195°–205° C. for 16 hours while blowing the mixture with nitrogen. An additional 755 parts of oil are then added, the mixture cooled to 140° C., and filtered. The filtrate is an oil solution of the desired ester.

EXAMPLE B-12

An ester is prepared by heating 658 parts of a carboxylic acid having an average molecular weight of 1018 (prepared by reacting chlorinated polyisobutene with acrylic acid) with 22 parts of pentaerythritol while maintaining a temperature of about 180°–205° C. for about 18 hours during which time nitrogen is blown through the mixture. The mixture is then filtered and the filtrate is the desired ester.

EXAMPLE B-13

To a mixture comprising 408 parts of pentaerythritol and 1100 parts oil heated to 120° C., there is slowly added 2946 parts of the acid of Example B-9 which has been preheated to 120° C., 225 parts of xylene, and 95 parts of diethyleneglycol dimethylether. The resulting mixture is heated at 195°–205° C., under a nitrogen atmosphere and reflux conditions for eleven hours, stripped to 140° C. at 22 mm. (Hg) pressure, and filtered. The filtrate comprises the desired ester. It is diluted to a total oil content of 40%.

In its broadest concept, the invention relates to two-cycle lubricants and lubricant-fuels containing the phenolic compounds (A). Such lubricant and lubricant fuels generally will contain from about one to 30 parts by weight of the phenolic compound per hundred parts of oil. In a preferred concept, the invention relates to further improved two-cycle lubricants and lubricant-fuel oils containing a mixture of the phenolic compounds (A) and the detergent/dispersants (B).

These oil compositions contain about one to about 30%, typically about 5 to about 20%, of at least one phenolic compound (A) as described hereinabove and about 1 to about 30%, typically 2 to about 20% of at least one detergent/dispersant (B). The weight ratio of phenol to detergent/dispersant in these oils varies between about 1:10 to about 10:1. Other additives such as viscosity index (VI) improvers, lubricity agents, antioxidants, coupling agents, pour point depressing agents, extreme pressure agent, color stabilizers and anti-foam agents can also be present.

Polymeric VI improvers have been and are being used as bright stock replacement to improve lubricant film strength and lubrication and/or to improve engine cleanliness. Dye may be used for identification purposes and to indicate whether a two-cycle fuel contains lubricant. Coupling agents such as organic surfactants are incorporated into some products to provide better component solubilities and improved fuel/lubricant water tolerance.

Anti-wear and lubricity improvers, particularly sulfurized sperm oil substitutes and other fatty acid and vegetable oils, such as castor oil, are used in special applications, such as racing and for very high fuel/lubricant ratios. Scavengers or combustion chamber deposit modifiers are sometimes used to promote better spark plug life and to remove carbon deposits. Halogenated compounds and/or phosphorus-containing materials may be used for this application.

Rust and corrosion inhibitors of all types are and may be incorporated into two-cycle oil formulations. Odorants or deodorants are sometimes used for aesthetic reasons.

Lubricity agents such as synthetic polymers (e.g., polyisobutene having a number average molecular weight in the range of about 750 to about 15,000, (as measured by vapor phase osmometry or gel permeation chromatography), polyol ether (e.g., poly(oxyethylene-oxypropylene)ethers) and ester oils (e.g., the ester oils described above) can also be used in the oil compositions of this invention. Natural oil fractions such as bright stocks (the relatively viscous products formed during conventional lubricating oil manufacture from petroleum) can also be used for this purpose. They are usually present in the two-cycle oil in the amount of about 3 to about 20% of the total oil composition.

Diluents such as petroleum maphthas boiling at the range of about 30°–90° (e.g., Stoddard solvent) can also be included in the oil compositions of this invention, typically in the amount of 5 to 25%.

Table B describes several illustrative two-cycle engine oil lubricant compositions of this invention.

TABLE B

TWO-CYCLE ENGINE OIL BLENDS

| Example | Phenol of Example A-1 | Detergent/Dispersant Example | Amount[1] | Oil[2] Amount, pbw |
|---|---|---|---|---|
| A | 6 | B-2 | 2 | 92 |
| B | 4.5 | B-2 | 1.5 | 94 |
| C | 10.6 | B-6 | 2.1 | 87.3 |
| D | 7.5 | B-4 | 3.5 | 89 |
| E | 6 | B-3 | 2 | 92 |
| F | 15 | B-5 | 3 | 82 |
| G | 14.2 | — | — | 85.8 |

[1] Part by weight of the oil solution described in the indicated Examples.
[2] The same base oil is used in each blend; this oil is a 650 neutral solvent extracted paraffinic oil cut with 20 percent by volume Stoddard solvent and containing 9 pbw per hundred parts of final blend of a bright stock having a viscosity of 150 SUS at 100° C.

In some two-cycle engines the lubricating oil can be directly injected into the combustion chamber along with the fuel or into the fuel just prior to the time the fuel enters the combustion chamber. The two-cycle lubricants of this invention can be used in this type of engine.

As is well known to those skilled in the art, two-cycle engine lubricating oils are often added directly to the fuel to form a mixture of oil and fuel which is then introduced into the engine cylinder. Such lubricant-fuel oil mixtures are within the scope of this invention. Such lubricant-fuel blends generally contain per 1 part of oil about 15–250 parts fuel, typically they contain 1 part oil to about 50–100 parts fuel.

The fuels used in two-cycle engines are well known to those skilled in the art and usually contain a major portion of a normally liquid fuel such as hydrocarbonaceous petroleum distillate fuel (e.g., motor gasoline as defined by ASTM Specification D-439-73). Such fuels can also contain non-hydrocarbonaceous materials such as alcohols, ethers, organonitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Examples of such fuel mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Two-cycle fuels also contain other additives which are well known to those of skill in the art. These can include anti-knock agents such as tetra-alkyl lead compounds, lead scavengers such as halo-alkanes (e.g., ethylene dichloride and ethylene dibromide), dyes, cetane improvers, anti-oxidants such as 2,6-di-tertiary-butyl-4-methylphenol, rust inhibitors, such as alkylated succinic acids and anhydrides, bacteriostatic agents, gum inhibitors, metal deactivators, demulsifiers, upper cylinder lubricants, antiicing agents and the like. The invention is useful with lead-free as well as lead-containing fuels.

An example of a lubricant-fuel composition encompassed by this invention is a blend of motor gasoline and the lubricant blend described above in Example C in ratio (by weight) of 50 parts gasoline to 1 part lubricant.

Concentrates containing the compositions of this invention are also within the scope of this invention. These concentrates usually comprise about 20 to about 80% of one or more of the hereinabove described oils and about 20 to about 80% of one or more phenolic compounds with and without the detergent/dispersants. As will be readily understood by those skilled in the art, such concentrates can also contain one or more of the hereinabove described auxiliary additives of various types. Illustrative of these inventive concentrates are the following:

EXAMPLE H

A concentrate for treating 2-cycle engine oils is prepared by blending at room temperature 78.2 parts of the oil solution described in Example A-1 with 21.8 parts of the oil solution described in Example B-2.

What is claimed is:

1. A lubricant composition for two-cycle engines comprising a major amount by weight of at least one oil of lubricating viscosity and a minor amount, sufficient to control piston ring sticking and promote general engine cleanliness, of (A) at least one phenolic compound of the formula

wherein R is a substantially saturated hydrocarbon-based group of an average at least 10 aliphatic carbon atoms; a and b are each independently an integer of one up to three times the number of aromatic nuclei present in Ar with the proviso that the sum of a and b does not exceed the unsatisfied valences of Ar; and Ar is a single ring, a fused or a linked polynuclear ring aromatic moiety having 0 to 3 optional substituents selected from the group consisting of lower alkyl, lower alkoxyl, halo and combinations of two or more of said optional substituents.

2. The composition of claim 1 wherein R contains an average of at least 30 and up to about 400 aliphatic carbon atoms.

3. The composition of claim 2 wherein R is derived from homopolymerized or interpolymerized $C_2$–$C_{10}$ olefins.

4. The composition of claim 1 wherein there are no optional substituents attached to Ar.

5. The composition of claim 1 wherein the phenolic compound (A) is an alkylated phenol of the formula

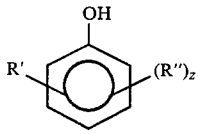

wherein R' is a substantially saturated hydrocarbon-based substituent having an average of from about 10 to about 400 aliphatic carbon atoms, R" is a member selected from the group consisting of lower alkyl, lower alkoxyl, and halo; and z is from 0 to 2.

6. The composition of claim 5 wherein z is 0.

7. The composition of claim 1 also containing a minor amount of a detergent/dispersant.

8. A lubricant composition for two-cycle engines comprising a major amount by weight of at least one oil of lubricating viscosity and a minor amount, sufficient to control piston ring sticking and promote general engine cleanliness, of
(A) at least one phenolic compound of the formula

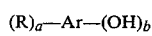

wherein R is a substantially saturated hydrocarbon-based group of an average of at least 10 aliphatic carbon atoms; a and b are each independently an integer of one up to three times the number of aromatic nuclei present in Ar with the proviso that the sum of a and b does not exceed the unsatisfied valences of Ar; and Ar is a single ring, a fused ring or a linked polynuclear aromatic moiety having 0 to 3 optional substituents selected from the group consisting of lower alkyl, lower alkoxyl, halo and combinations of two or more of said optional substituents; and
(B) at least one detergent-dispersant selected from the group consisting of
  i. at least one neutral or basic metal salt of an organic sulfur acid, phenol or carboxylic acid;
  ii. at least one hydrocarbyl-substituted amine wherein the hydrocarbyl substituent is substantially aliphatic and contains at least 12 carbon atoms;
  iii. at least one acylated, nitrogen-containing compound having a substituent of at least 10 aliphatic carbon atoms made by reacting a carboxylic agant with at least one amino compound containing at least one

—NH— group, said acylating agent being linked to said amino compound through an imido, amido, amidine, or acyloxy ammonium linkage;
  iv. at least one nitrogen-containing condensate of a phenol, aldehyde and amino compound having at least one

—NH— group; and
  v. at least one ester of a substituted polycarboxylic acid.

9. The composition of claim 8 wherein R contains an average of at least 30 and up to about 400 aliphatic carbon atoms.

10. The composition of claim 8 wherein there are no optional substituents attached to Ar.

11. The composition of claim 8 wherein a and b each are 1.

12. The composition of claim 8 wherein the phenolic compound (A) is an alkylated phenol of the formula

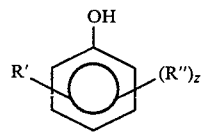

wherein R' is a substantially saturated hydrocarbon-based substituent having an average of from about 10 to about 400 aliphatic carbon atoms, R" is a member selected from the group consisting of lower alkyl, lower alkoxyl, and halo; and z is 0 to 2.

13. The composition of claim 12 wherein R' is a purely hydrocarbyl aliphatic group of at least about 50 carbon atoms and is derived from a polymer or interpolymer of an olefin selected from the group consisting of $C_2$-$C_{10}$ 1-mono olefins and mixtures thereof.

14. The composition of claim 13 wherein z is 0.

15. The composition of claim 8 wherein the detergent/dispersant is at least one alkaline earth metal sulfonate.

16. The composition of claim 15 wherein the sulfonate is an alkyl-substituted benzene sulfonate wherein the alkyl group has at least about 8 carbon atoms.

17. The composition of claim 8 wherein the detergent/dispersant is at least one hydrocarbyl-substituted amine.

18. The composition of claim 8 wherein the detergent/dispersant is (iii) at least one acylated, nitrogen-containing compound having a substituent of at least 10 aliphatic carbon atoms and made by reacting a carboxylic acylating agent with at least one amino compound containing at least one

—NH— group, said acylating agent being linked to said amino compound through an imido, amido, amidine or acyloxy ammonium linkage.

19. The composition of claim 18 wherein the amino compound is an alkylene polyamine of the general formula

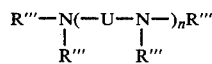

wherein U is an alkylene group of 2 to 10 carbon atoms; each R''' is independently a hydrogen atom, a lower alkyl group or a lower hydroxy alkyl group, with the proviso that at least one R''' is a hydrogen atom, ann n is 1 to 10.

20. The composition of claim 19 wherein the acylating agent is a mono or polycarboxylic acid, or reactant equivalent thereof, containing an aliphatic hydrocarbyl substituent of at least about 30 carbon atoms.

21. The composition of claim 8 wherein the ratio by weight of phenol to the total amount of detergent/dispersant is in the range of about 1:10 to about 10:1.

22. In the method for lubricating a two-cycle internal combustion engine, the improvement which comprises using a lubricant composition as claimed in claim 1.

23. In the method for lubricating a two-cycle internal combustion engine, the improvement which comprises using a lubricant composition as claimed in claim 7.

24. In the method for lubricating a two-cycle internal combustion engine, the improvement which comprises using the lubricant composition of claim 8.

25. A lubricant-fuel mixture for use in two-cycle internal combustion engines wherein the lubricant is the composition of claim 1.

26. A lubricant-fuel mixture for use in two-cycle internal combustion engines wherein the lubricant is the composition of claim 8.

* * * * *